(12) United States Patent
Slaughter et al.

(10) Patent No.: US 10,531,878 B2
(45) Date of Patent: Jan. 14, 2020

(54) ATRIAL APPENDAGE CLOSURE DEVICE AND RELATED METHODS

(71) Applicant: University of Louisville Research Foundation, Inc., Louisville, KY (US)

(72) Inventors: Mark S. Slaughter, Louisville, KY (US); Guruprasad A. Giridharan, Louisville, KY (US); Steven C. Koenig, Floyds Knobs, IN (US); Michael A. Sobieski, Floyds Knobs, IN (US); Kevin Soucy, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 813 days.

(21) Appl. No.: 14/417,536

(22) PCT Filed: Jul. 26, 2013

(86) PCT No.: PCT/US2013/052362
§ 371 (c)(1),
(2) Date: Jan. 26, 2015

(87) PCT Pub. No.: WO2014/018907
PCT Pub. Date: Jan. 30, 2014

(65) Prior Publication Data
US 2015/0250482 A1 Sep. 10, 2015

Related U.S. Application Data

(60) Provisional application No. 61/676,157, filed on Jul. 26, 2012, provisional application No. 61/791,147, filed on Mar. 15, 2013.

(51) Int. Cl.
*A61B 17/12* (2006.01)
*A61B 17/00* (2006.01)
*A61B 17/122* (2006.01)

(52) U.S. Cl.
CPC .. *A61B 17/12122* (2013.01); *A61B 17/12036* (2013.01); *A61B 17/12172* (2013.01);
(Continued)

(58) Field of Classification Search
CPC ........ A61B 17/12036; A61B 17/12122; A61B 17/12172; A61B 17/12177; A61B 17/122;
(Continued)

(56) References Cited

U.S. PATENT DOCUMENTS 5,725,552 A 3/1998 Kotula et al.
5,846,261 A 12/1998 Kotula et al.
(Continued)

FOREIGN PATENT DOCUMENTS

WO 2001030267 A1 5/2001
WO 2007044536 4/2007
(Continued)

OTHER PUBLICATIONS

European Patent Office, Supplementary European Search Report, issued in corresponding Application No. EP 13823446, dated Mar. 2, 2016.
(Continued)

*Primary Examiner* — George J Ulsh
(74) *Attorney, Agent, or Firm* — W&C IP

(57) ABSTRACT

An atrial appendage closure device is provided that includes an insertion rod having a first end and a second end. An occluding member having an outer surface and an inner surface is connected to the first end of the insertion rod. The occluding member is moveable between a retracted position and a deployed position such that, in the deployed position, the occluding member is configured to provide a seal between a left atrial appendage and a left atrium of a heart. An anchoring member is further connected to the insertion rod and is configured to slide along the insertion rod to secure the device to a wall of a left atrial appendage. Methods for occluding a left atrial appendage that make use of the closure devices are also provided.

15 Claims, 13 Drawing Sheets

(52) U.S. Cl.
CPC ...... *A61B 17/12177* (2013.01); *A61B 17/122* (2013.01); *A61B 2017/00247* (2013.01); *A61B 2017/1205* (2013.01); *A61B 2217/005* (2013.01)

(58) Field of Classification Search
CPC .. A61B 2017/00247; A61B 2017/1205; A61B 2217/005; A61B 17/08; A61B 17/12; A61F 2/24
See application file for complete search history.

(56) References Cited

U.S. PATENT DOCUMENTS

| | | | |
|---|---|---|---|
| 6,506,204 | B2 | 1/2003 | Mazzocchi |
| 6,551,303 | B1 | 4/2003 | Van Tassel et al. |
| 6,652,555 | B1 | 11/2003 | Van Tassel et al. |
| 6,652,556 | B1 | 11/2003 | Van Tassel et al. |
| 6,689,150 | B1 | 2/2004 | Van Tassel et al. |
| 6,730,108 | B2 | 5/2004 | Van Tassel et al. |
| 6,949,113 | B2 | 9/2005 | Van Tassel et al. |
| 7,288,105 | B2 | 10/2007 | Oman et al. |
| 7,377,936 | B2 | 5/2008 | Gainor et al. |
| 7,566,336 | B2 | 7/2009 | Corcoran et al. |
| 7,727,189 | B2 | 6/2010 | Van Tassel et al. |
| 8,080,032 | B2 | 12/2011 | van der Burg et al. |
| 8,100,938 | B2 | 1/2012 | Figulla et al. |
| 8,221,445 | B2 | 7/2012 | Van Tassel et al. |
| 8,372,113 | B2 | 2/2013 | Opolski |
| 8,685,055 | B2 | 4/2014 | Van Tassel et al. |
| 8,696,693 | B2 | 4/2014 | Najafi et al. |
| 8,715,300 | B2 | 5/2014 | Najafi et al. |
| 8,758,389 | B2 | 6/2014 | Glimsdale |
| 8,777,974 | B2 | 7/2014 | Amplatz et al. |
| 8,784,448 | B2 | 7/2014 | Chanduszko |
| 8,821,529 | B2 | 9/2014 | Kariniemi et al. |
| 2004/0230222 | A1 | 11/2004 | van der Burg et al. |
| 2005/0004652 | A1 | 1/2005 | van der Burg et al. |
| 2005/0049573 | A1 | 3/2005 | Van Tassel et al. |
| 2005/0070952 | A1 | 3/2005 | Devellian |
| 2006/0122646 | A1* | 6/2006 | Corcoran ........... A61B 17/0057 606/213 |
| 2008/0033241 | A1 | 2/2008 | Peh et al. |
| 2009/0099596 | A1 | 4/2009 | McGuckin, Jr. et al. |
| 2009/0228038 | A1 | 9/2009 | Amin |
| 2010/0191279 | A1 | 7/2010 | Kassab et al. |
| 2010/0228279 | A1 | 9/2010 | Miles et al. |
| 2011/0082495 | A1 | 4/2011 | Ruiz |
| 2011/0178539 | A1 | 7/2011 | Holmes, Jr. et al. |
| 2011/0218566 | A1 | 9/2011 | van der Burg et al. |
| 2012/0065662 | A1 | 3/2012 | van der Burg et al. |
| 2012/0065667 | A1 | 3/2012 | Javois et al. |
| 2012/0172927 | A1 | 7/2012 | Campbell et al. |
| 2012/0283585 | A1 | 11/2012 | Werneth et al. |
| 2012/0283773 | A1 | 11/2012 | Van Tassel et al. |
| 2013/0030455 | A1 | 1/2013 | Venkatraman et al. |
| 2013/0046254 | A1 | 2/2013 | Venkatraman et al. |
| 2013/0067188 | A1 | 3/2013 | Mehra et al. |
| 2013/0165967 | A1 | 6/2013 | Amin et al. |
| 2013/0296925 | A1 | 11/2013 | Chanduszko et al. |
| 2013/0338686 | A1 | 12/2013 | Ruiz |
| 2014/0046347 | A1 | 2/2014 | Cully et al. |
| 2014/0207153 | A1 | 7/2014 | Najafi et al. |
| 2014/0214077 | A1 | 7/2014 | Glimsdale |
| 2014/0257360 | A1 | 9/2014 | Keillor |
| 2014/0257361 | A1 | 9/2014 | Prom |
| 2014/0288591 | A1 | 9/2014 | Amplatz et al. |

FOREIGN PATENT DOCUMENTS

| | | |
|---|---|---|
| WO | 2008125689 | 10/2008 |
| WO | 20080150346 | 12/2008 |
| WO | 2010006061 | 1/2010 |
| WO | 20100006061 A2 | 1/2010 |

OTHER PUBLICATIONS

European Patent Office, Examination Report issued in corresponding Application No. 13 823 446.3, dated Apr. 7, 2017.
AtriClip™ LAA Exclusion System with PreloadedGillinov-Cosgrove™ Clip.
Singh SM, et al. Percutaneous Left Atrial Appendage Closure with an Epicardial Suture Ligation Approach: A Prospective Randomized Pre-Clinical Feasibility Study. Mar. 2010.
Friedman PA, et al. Percutaneous Epicardial Left Atrial Appendage Closure: Preliminary Results of an Electrogram Guided Approach. Aug. 2009.
Cruz-Gonzalez I, et al. Left Atrial Appendage Exclusion Using an Amplatzer Device. May 2009.
Macdonald ST, et al. Intracardiac Echocardiography off Piste? Closure of the Left Atrial Appendage Using ICE and Local Anesthesia. Jan. 1, 2011.
Moreira-Pinto J., et al. Left Atrial Appendage Ligation with Single Transthoracic Port Assistance: A Study of Survival Assessment in a Porcine Model (With Videos). May 2012.
Atrial Fibrillation Fact Sheet. Feb. 2010. Centers for Disease Control and Prevention. Apr. 3, 2012.
Go AS, Hylek EM, Phillips KA, Chang Y, Henault LE, Shelby JV and Singer DE. Prevalence of Diagnosed Atrial Fibrillation in Adults: National Implications for Rhythm Management and Stroke Prevention: the Anticoagulation and Risk Factors in Atrial Fibrillation (Atria) Study. Journal of the American Medical Association 2001;285:2370-2375.
Wolf PA, Abbott RD, and Kannel WB. Atrial fibrillation as an Independent factor for stroke: The Framingham study. Stroke; 1991; 22:983-988.
Pearce LA, Hart RG and Halperin JL. Assessment of Three Schemes for Stratifying Stroke Risk in Patients with Nonvalvular Atrial Fibrillation. The American Journal of Medicine 2000;109:45-51.
Aronow WS. Management of the Older Person With Atrial Fibrillation. Journal of Gerontology: Medical Sciences 2002;57A:M352-M363.
Savelieva I, Bajpai A and Camm AJ. Stroke in atrial fibrillation: Update on pathophysiology, new antithrombotic therapies, and evolution of procedures and devices. Annals of Medicine 2007;39:371-391.
Jais P, Haissaguerre M, Shah DC, Chouairi S, Gencel L, Hocini M, and Clementy J. A Focal Source of Atrial Fibrillation Treated by Discrete Radiofrequency Ablation. Circulation. 1997;95:572-576.
Go AS, Hylek EM, Borowsky LH, Phillips KA, Selby JV and Singer DE. Warfarin Use among Ambulatory Patients with Nonvalvular Atrial Fibrillation: The Anticoagulation and Risk Factors in Atrial Fibrillation (Atria) Study. Annals of Internal Medicine 1999;131:927-934.
Mendelson G, and Aronow WS. Underutilization of Warfarin in Older Persons with Chronic Nonvalvular Atrial Fibrillation at High Risk for Developing Stroke. Journal of the American Geriatrics Society 1998;46:p. 1423-p. 1424.
Hart RG, Benavente O, Mcbride R and Pearce LA. Antithrombotic Therapy to Prevent Stroke in Patients with Atrial Fibrillation: A Meta-Analysis. Annals of Internal Medicine 1999;131:492-501.
Hylek EM, Go AS, Chang Y, Jensvold NG, Henault LE, Selby JV, et al. Effect of intensity of oral anticoagulation on stroke severity and mortality in atrial fibrillation. N Engl J Med. 2003;349:1019-26.
Nieuwlaat R, Capucci A, Lip GY, Olsson SB, Prins MH, Nieman FH, et al.; Euro Heart Survey Investigators. Antithrombotic treatment in real-life atrial fibrillation patients: a report from the Euro Heart Survey on Atrial Fibrillation. Eur Heart J. 2006;27:3018-26.
McCormick D, Gurwitz JH, Goldberg RJ, Becker R, Tate JP, Elwell A, et al. Prevalence and quality of warfarin use for patients with atrial fibrillation in the long-term care setting. Arch Intern Med. 2001;16:2458-63.
Sarawate C, Sikirica MV, Willey VJ, Bullano MF, Hauch O. Monitoring anticoagulation in atrial fibrillation. J Thromb Thrombolysis. 2006;21:191-8.

(56) References Cited

OTHER PUBLICATIONS

Singer DE, Albers GW, Dalen JE, Go AS, Halperin JL, and Manning WJ. Antithrombotic therapy in atrial fibrillation: the Seventh ACCP Conference on Antithrombotic and Thrombolytic Therapy. Chest 2004;126:429S-56S.
Risk factors for stroke and efficacy of antithrombotic therapy in atrial fibrillation. Analysis of pooled data from five randomized controlled trials. Archives of Internal Medicine 1994;154:1449-57.
Atwood JE, and Albers GW. Anticoagulation and atrial fibrillation. Herz 1993;18:27-38.
Gullov AL, Koefoed BG, and Petersen P. Bleeding During Warfarin and Aspirin Therapy in Patients With Atrial Fibrillation: The Afasak 2 Study. Archives of Internal Medicine 1999;159:1322-1328.
Liu M, Counsell C, Sandercock P. Anticoagulants for preventing recurrence following ischaemic stroke or transient ischaemic attack. (Cochrane Review). In: The Cochrane Library, Issue 1, 2002. Oxford: Update Software.
Desbiens DA. Deciding on Anticoagulating the Oldest Old with Atrial Fibrillation: Insights from Cost-Effectiveness Analysis. JAGS 2002;50:863-869.
Aronow WS, Ahn C, Kronzon I, and Gutstein H. Incidence of new thromboembolic stroke in persons 62 years and older with chronic atrial fibrillation treated with warfarin versus aspirin. Journal of the American Geriatrics Society 1999;47:366-8.
Lip GYH. Aspirin for Prevention of Stroke in Atrial Fibrillation. Stroke 2006;37:1640.
Garcia D, and Hylek E. Stroke prevention in elderly patients with atrial fibrillation. The Lancet 2007;370:460-461.
Lip GYH and Boos CJ. Antithrombotic treatment in atrial fibrillation. Heart 2006;92:155-161.
Jaffer AK. Warfarin reduced major stroke more than aspirin in elderly patients with atrial fibrillation in primary care. Evidence Based Medicine 2007;12:172.
Kamath S, Blann AD, Chin BS, Lip GYH. A prospective randomized trial of aspirin-clopidogrel combination therapy and dose-adjusted warfarin on indices of thrombogenesis and platelet activation in atrial fibrillation. J Am Coll Cardiol. 2002;40:484-90.
Lorenzoni R, Lazzerini G, Cocci F, DE Caterina R. Shortterm prevention of thromboembolic complications in patients with atrial fibrillation with aspirin plus clopidogrel: the Clopidogrel-Aspirin Atrial Fibrillation (CLAAF) pilot study. Am Heart J. 2004;148:e6.
Active Writing Group on behalf of the Active Investigators; Connolly S, Pogue J, Hart R, Pfeffer M, Hohnloser S, Chrolavicius S, et al. Clopidogrel plus aspirin versus oral anticoagulation for atrial fibrillation in the Atrial fibrillation Clopidogrel Trial with Irbesartan for prevention of Vascular Events (ACTIVE W): a randomized controlled trial. Lancet. 2006;367:1903-12.
Healey J, Hart R, Pogue J, Yusuf S, Pfeffer M, Hohnloser S, et al., on behalf of The ACTIVE-W Investigators. Effect of underlying risk of stroke on treatment effects in the ACTIVEW Trial. (Abstract). Eur Heart J. 2006;27 Supplement: Abstract P451.
Perzborn E, Roehrig S, Straub, A, Dagmar K, Mueck W, and Laux V. Rivaroxaban: A new oral factor Xa inhibitor. Arteriosclerosis, Thrombosis, and Vascular Biology. 2010;30:376-381.
Eriksson B, Quinlan D, Weitz J. Comparative Pharmacodynamics and Pharmacokinetics of oral direct thrombin and Factor Xa inhibitors in development. Clinical Pharmacokinetics 2009: 48: 1-22.
Bayard YL, Ostermayer SH, Hein R, Skowasch M, Buscheck F, Baranowski A, Heinisch C, Sievert H. Percutaneous devices for stroke prevention. Cardiovascular Revascularization Medicine. 2007:8:216-225.

Hanna IR, Kolm P, Martin R, Reisman M, Gray W and Block PC. Left atrial structure and function after percutaneous left atrial appendage transcatheter occlusion (PLAATO): Six-month echocardiographic follow-up. Journal of the American College of Cardiology 2004;43:1868-72.
Nakai T, Lesh MD, Gerstenfeld EP, Virmani R, Jones R and Lee RJ. Percutaneous Left Atrial Appendage Occlusion (PLAATO) for Preventing Cardioembolism: First Experience in Canine Model. Circulation 2002;105:2217-2222.
Ostermayer SH, et al. Percutaneous Left Atrial Appendage Transcatheter Occlusion (PLAATO System) to Prevent Stroke in High-Risk Patients With Non-Rheumatic Atrial Fibrillation: Results From the International Multi-Center Feasibility Trials. Journal of the American College of Cardiology 2005;46:9-14.
Sievert H, Lesh MD, Trepels T, Omran H, Bartorelli A, Bella PD, Nakai T, Reisman M, Dimario C, Block P, Kramer P, Fleschenberg D, Krumsdorf U, and Scherer D. Percutaneous Left Atrial Appendage Transcatheter Occlusion to Prevent Stroke in High-Risk Patients With Atrial Fibrillation: Early Clinical Experience. Circulation 2002;105:1887-1889.
Fountain RB, Holmes DR, Chandrasekaran K, Packer D, Asirvatham S, Tassel RV and Turi Z. The Protect AF (Watchman Left Atrial Appendage System for Embolic Protection in Patients with Atrial Fibrillation) Trial. American Heart Journal 2006;151:956-61.
Sick PB, Schuler G, Hauptmann KE, Grube E, Yakubov S, Turi ZG, Mishkel G, Almany S, and Holmes DR. Initial Worldwide Experience with the Watchman Left Atrial Appendage System for Stroke Prevention in Atrial Fibrillation. Journal of the American College of Cardiology 2007;49:1490-5.
Sievert H and Bayard YL. Percutaneous closure of the left atrial appendage: A major step forward. J Am Coll Cardiol Intv, 2009; 2:601-602.
Block PC. Watching the Watchman. J Am Coll Cardiol, 2007; 49:1496-1497.
Maisel WH. Left atrial appendage occlusion—closure or just the beginning. New England Journal of Medicine, 2009.
Onalan O and Crystal E. Left Atrial Appendage Exclusion for Stroke Prevention in Patients With Nonrheumatic Atrial Fibrillation. Stroke 2007;38:624-630.
Ailawadi G, Gerdisch MW, Harvey RL, Hooker RL, Damiano RJ Jr, Salamon T, and Mack MJ. Exclusion of the left atrial appendage with a novel device: early results of a multicenter trial. J Thorac Cardiovasc Surg. 2011;142(5):1002-9.
Payne KA, Huybrechts KF, Caro JJ, Craig Green TJ, Klittich WS. Long term cost-of-illness in stroke: an international review. Pharmacoeconomics. 2002;20:813-25.
Lafata JE, Martin SA, Kaatz S, Ward RE. The cost effectiveness of different management strategies for patients on chronic warfarin therapy. J Gen Intern Med. 2000;15:31-7.
Amplatzer® AtrialSeptal Occluder. May 24, 2012.
Montenegro MJ, et al. Percutaneous Occlusion of Left Atrial Appendage with the Amplatzer Cardiac Plugtmin Atrial Fibrillation. Jan. 31, 2012.
The WaveCrest Solution. 2014.
Mobius-Winkler S, et al. The Watchman Left Atrial Appendage Closure Device for Atrial Fibrillation. Feb. 28, 2012.
Watchman LAA Closure procedure. 2010.
IP Australia, Patent Examination Report No. 1 issued in corresponding Application No. 2013295524, dated Nov. 28, 2016.

* cited by examiner

ATRIAL APPENDAGE CLOSURE DEVICE AND RELATED METHODS

RELATED APPLICATIONS

This application claims priority from U.S. Provisional Application Ser. Nos. 61/676,157, filed Jul. 26, 2012, and 61/791,147, filed Mar. 15, 2013, the entire disclosures of which are incorporated herein by this reference.

TECHNICAL FIELD

The presently-disclosed subject matter relates to an atrial appendage closure device. In particular, the presently-disclosed subject matter relates to an atrial appendage closure device having an insertion rod and an occluding member, which, in a deployed position, is configured to provide a seal between a left atrial appendage and a left atrium of a heart.

BACKGROUND

In the United States, there are approximately three million patients with atrial fibrillation (AF), and this number is expected to increase to five million by 2040. AF is an irregular sinus rhythm and atrial dysrhythmia, which results in a rapid, irregular, and unsynchronized contraction of the atrium. In AF, blood is not washed from the left atrial appendage and it stagnates and tends to clot inside the heart. However, these clots are prone to leaving the heart and embolizing to different organs in the body. For example, it has been observed that the clots frequently leave the heart and enter the cerebral vessels, resulting in an embolic stroke. Indeed, patients with AF are at a significantly increased risk of stroke, and it is estimated that patients with AF have, on average, 5 to 6 times greater probability of having a stroke (5-15% annualized risk of stroke) and 18 times greater probability of having an embolic event. This risk of stroke with AF only increases with age, with up to 30% of all strokes in elderly patients occurring due to AF, and with, overall, at least 100,000 strokes per year being attributed to AF in the United States alone.

Medical and ablation therapies have been used to attempt to eliminate AF, but most patients continue to remain in AF after therapy. In this regard, current treatment of AF often includes anticoagulation therapy with warfarin, which has been reported to reduce the risk of stroke by 62%, but requires close monitoring to prevent bleeding complications that may otherwise result in mortality. In fact, even with close attention to warfarin dosing, life-threatening bleeding complications, intracerebral bleeding, or death still occurs in 1-2.5% of these patients every year, with the highest risk of warfarin complications being in elderly patients, who are also at the highest risk of stroke due to AF. Due to this risk, it is estimated that 40% to 65% of elderly patients with AF and at an increased risk of stroke are not receiving anticoagulant therapy with warfarin. However, it has further been estimated that 35% of patients with AF who are not treated with anticoagulants will likely have a stroke during their lifetime.

Antiplatelet therapy with aspirin has been proposed as a possible alternative to warfarin therapy, but to date has not proven to be very effective. Similarly, combination therapy with aspirin and clopidogrel has also not proven to be as effective in preventing clot formation as warfarin. New pharmaceutical agents aimed at factor Xa and thrombin inhibition anticoagulant agents, such as Pradaxa® (Boehringer Ingelheim Pharma GmbH & Co. KG; dabigatran etexilate) have provided similar reductions in stroke rates and less monitoring when compared to warfarin. Nevertheless, many of these agents, including Pradaxa® are contraindicated for patients over 75, have been shown to still result in bleeding complications, and still require compliance from elderly patients who often forget to take their oral medications.

To overcome these limitations of pharmaceutical agent-based therapies for treating AF, catheter-based left atrial appendage occluder devices, such as AMPLATZER® (AGA Medical Corporation), PLAATO® (EV3 Inc.), and WATCHMAN® (Atritech, Inc.), as well as other devices such as the TIGERPAW® system (LAAx, Inc.) and ATRICLIP® (AtriCure, Inc.), have recently been developed. Initial reports regarding the use of these device-based therapies to block the left atrial appendage have provided good results, and have shown that the devices can reduce hemorrhagic stroke as compared to warfarin therapy. However, recent clinical trials with these devices have also shown an associated increase in ischemic stroke, which is in addition to the fact that the implantation of the devices requires a delivery catheter to puncture the atrial septum as well as barbs for anchoring the devices, both of which can lead to several complications including puncturing of the left atrium. Moreover, these current left atrial appendage closure devices are not always completely effective in sealing off the left atrial appendage due to patient-to-patient variability in left atrial appendage sizes, thus leading to embolic clots. Further, it is also possible that any foreign material in the left atrial appendage may also cause thrombus formation. Accordingly, an atrial appendage closure device that avoids the adverse events common with current catheter-based left atrial appendage occluder devices or common with current pharmaceutical therapies would be both highly-desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes an atrial appendage closure device. In particular, the presently-disclosed subject matter includes an atrial appendage closure device having an insertion rod and an occluding member, which, in a deployed position, is configured to provide a seal between a left atrial appendage and a left atrium of a heart.

In one exemplary embodiment of the presently-disclosed subject matter, an atrial appendage closure device is provided that comprises an insertion rod having a first end and a second end. The atrial appendage closure device further includes an occluding member that is connected to the first end of the insertion rod. The occluding member includes an outer surface and an inner surface. Also included in the atrial appendage closure device is an anchoring member that is connected to or otherwise attached to the insertion rod for securing the device to a wall of the left atrial appendage.

The insertion rods of the exemplary atrial appendage closure devices are generally constructed from a metal or plastic material to provide an insertion rod having a sufficient amount of strength to allow it to be inserted into the wall of an atrial appendage of a heart and retain its shape. In this regard, the insertion rod can be in the form of a solid insertion rod (e.g., a wire) or can be in the form of a tube-like structure where the insertion rod defines a hollow interior cavity and an opening at the second end of the insertion rod. In some embodiments, such a hollow insertion rod can further define a plurality of fenestrations that are in fluid communication with the hollow interior cavity and the opening at the second end of the insertion rod, such that, upon using the occluding member to seal off a left atrial appendage, the fenestrations can be used to remove blood or fluid from the left atrial appendage.

With regard to the occluding member, the occluding member is moveable between a retracted position and a deployed position. The occluding member is typically comprised of a flexible material or membrane that is supported by a plurality of ribs radiating from the center of the occluding member to thereby provide a flexible structure that is capable of being moved between the retracted position and the deployed position. In the retracted position, the occluding member is positioned adjacent to and extends along the length of the first end of the insertion rod. In the deployed position, however, the occluding member generally assumes an umbrella-like shape, such that the occluding member is then configured to provide a seal between a left atrial appendage and a left atrium of a heart. In this regard, in some embodiments, in a deployed position, the outer surface of the occluding member assumes a concave shape and the inner surface of the occluding member assumes a convex shape. In other embodiments, in a deployed position, the outer surface of the occluding member assumes a convex shape and the inner surface of the occluding member assumes a flattened shape. In some embodiments, to further assist in sealing off the left atrial appendage from the left atria of a heart, the occluding member further includes a hooked portion at each end of the outer surface of the occluding member.

To further facilitate the use of the atrial appendix closure devices of the presently-disclosed subject matter and promote the integration of the devices into the heart of a subject, the outer surface, the inner surface, or both the outer surface and the inner surface of the occluding member are coated with an extracellular matrix. In some embodiments, to facilitate the use of the devices and promote their integration, the outer surface, the inner surface, or both the outer surface and the inner surface of the occluding member are coated with a growth factor.

With regard to the anchoring members included in the exemplary atrial appendage closure devices of the presently-disclosed subject matter, each anchoring member is generally connected to and configured to slide along the insertion rod. In certain embodiments, the anchoring member is in the form of a bolt that can be slid along the insertion rod and against the wall of an atrial appendage before being locked in place to secure the device to the wall of the left atrial appendage. In other embodiments, and similar to the occluding member, the anchoring member is movable between a retracted position and a deployed position, and has an umbrella-like shape with the proximal surface of the anchoring member being flat and the distal surface of the anchoring member having a convex shape.

Further provided by the presently-disclosed subject matter are methods of occluding a left atrial appendage. In one exemplary implementation of a method of occluding a left atrial appendage, a closure device is first provided that includes: an insertion rod having a first end and a second end; and an occluding member that has an outer surface and an inner surface and is connected to the first end of the insertion rod, with the occluding member being moveable between a retracted position and a deployed position. Upon providing the closure device, the occluding member and a portion of the insertion rod is then inserted into the left atrial appendage and into a left atrium of a heart by piercing the wall of the left atrial appendage and inserting the occluding member and the portion of the insertion rod while the occluding member is in a retracted position. Once inserted, the occluding member is then deployed inside the left atrium, such that the occluding member is now configured to provide a seal between the left atrial appendage and the left atrium of the heart. Subsequently, the inner surface of the occluding member is pulled toward the tip of the left atrial appendage, and the left atrial appendage is collapsed against and secured to the inner surface of the occluding member. In certain implementations that make use of an anchoring member in the closure devices, securing the inner surface of the occluding member against the wall of the left atrial appendage is then further accomplished by securing the anchoring member against the wall of the left atrial appendage opposite the inner surface of the occluding member to thereby provide a seal between a left atrial appendage and the left atrium of the heart.

Further features and advantages of the presently-disclosed subject matter will become evident to those of ordinary skill in the art after a study of the description, figures, and non-limiting examples in this document.

DESCRIPTION OF EXEMPLARY EMBODIMENTS

The presently-disclosed subject matter is an atrial appendage closure device and, more particularly, an atrial appendage closure device having an insertion rod and an occluding member, which, in a deployed position, is configured to occlude and provide a seal between a left atrial appendage and a left atrium of a heart.

Figure 1:
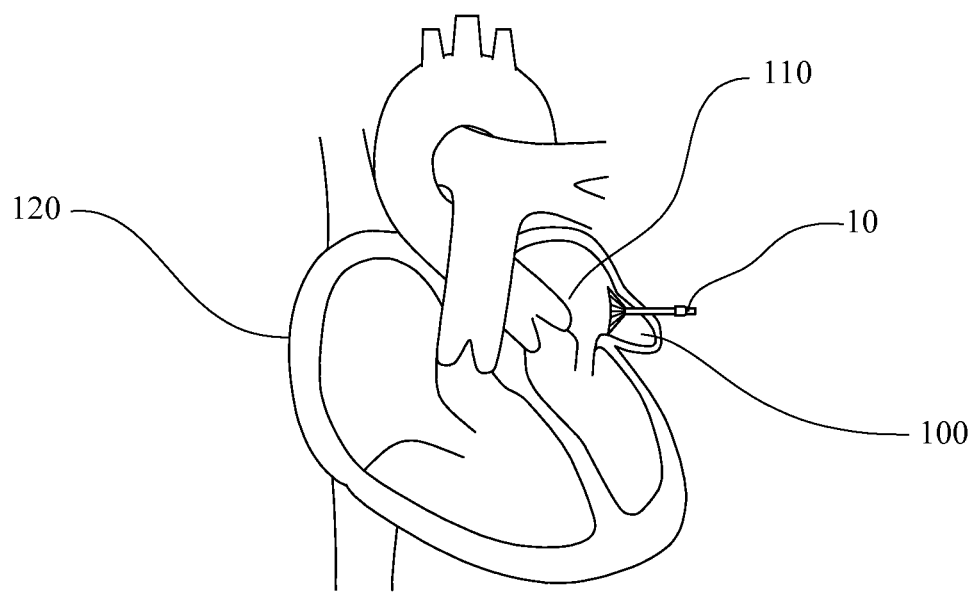
FIG. 1 is a schematic representation of a cross-section of a human heart showing an atrial appendage closure device made in accordance with the presently-disclosed subject matter and inserted into the left atrial appendage of the heart.
Figure 2A:
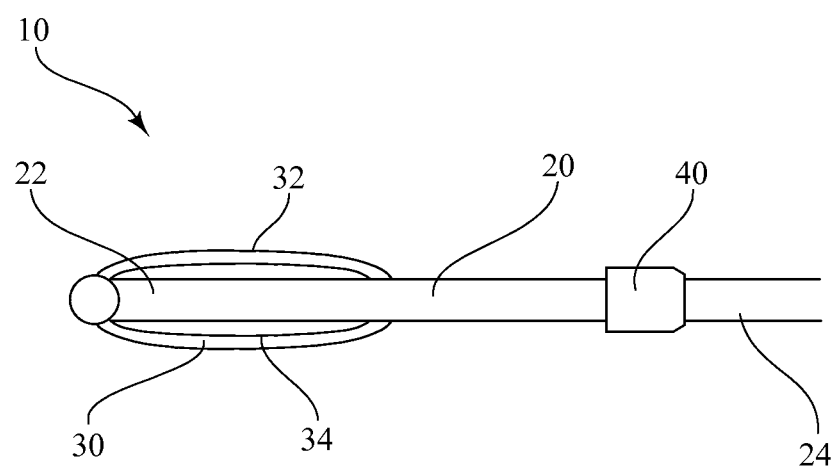
FIGS. 2A-2B are side views of an atrial appendage closure device made in accordance with the presently-disclosed subject matter, and showing the device in a retracted position (FIG. 2A) and in a deployed position (FIG. 2B)
Figure 2B:
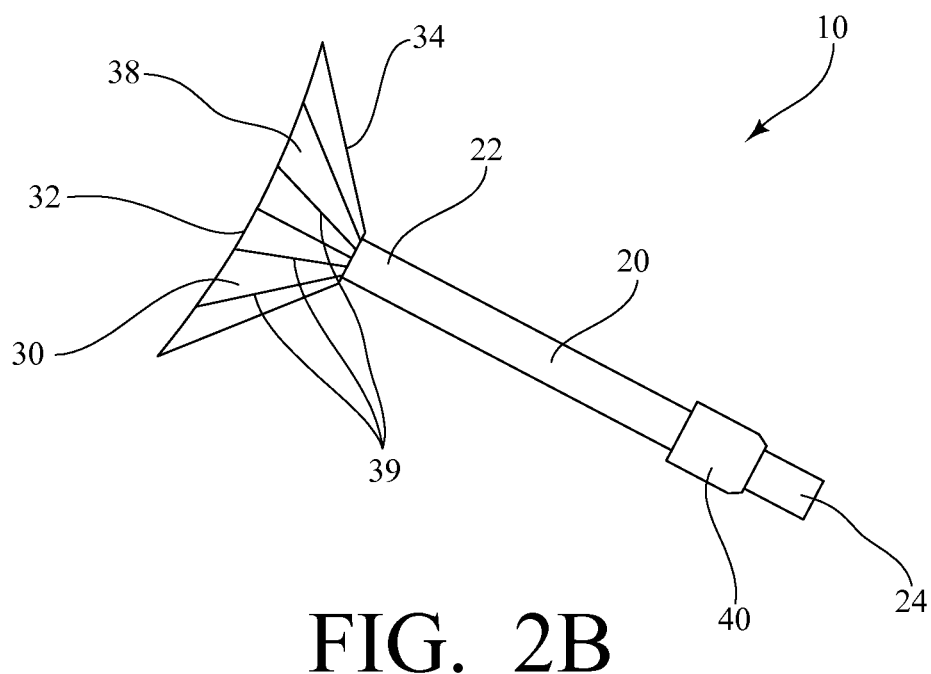

Referring first to FIG. 1 and FIGS. 2A-2B, an exemplary atrial appendage closure device 10 made in accordance with the presently-disclosed subject matter includes an insertion rod 20 having a first end 22 and a second end 24. The atrial appendage closure device 10 further includes an occluding member 30 that is connected to the first end 22 of the insertion rod 20. The occluding member 30 includes an outer surface 32 and an inner surface 34. Also included in the atrial appendage closure device 10 is an anchoring member 40 in the form of a bolt that is connected to or otherwise attached to the insertion rod 20 for securing the device 10 to the left atrial appendage 100 of a heart 120.

Figure 7:
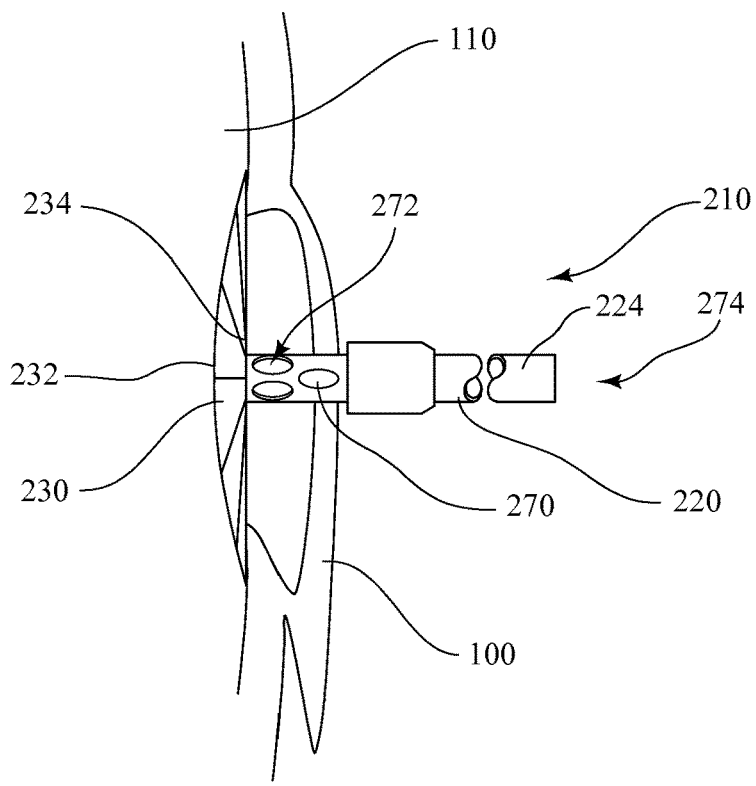
FIG. 7 is a schematic representation of another exemplary method of occluding a left atrial appendage in accordance with the presently-disclosed subject matter, in which another atrial appendage closure device of the presently-disclosed subject matter is used to collapse a left atrial appendage.
Figure 8:
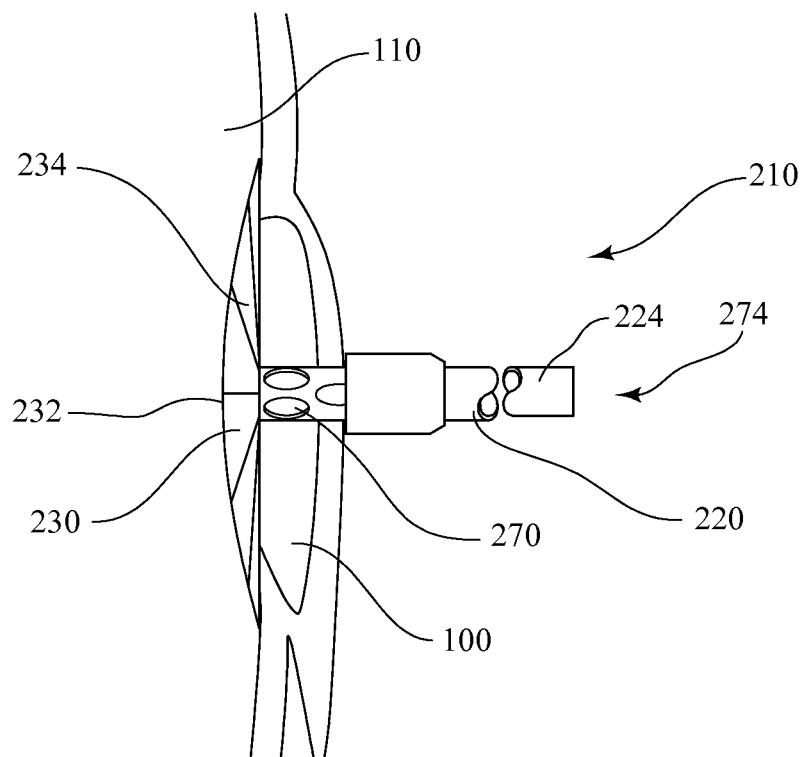
FIG. 8 is a schematic representation similar to FIG. 7, but further showing the left atrial appendage fully collapsed.
Figure 9:
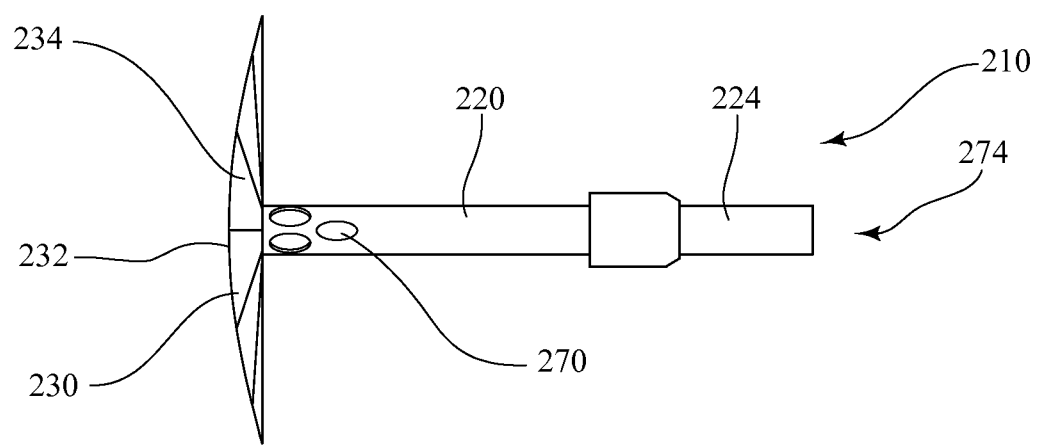
FIG. 9 is a side view of the left atrial appendage closure device used in accordance with the methods depicted in FIGS. 7 and 8.

With regard to the occluding member 30, and referring more specifically now to FIGS. 2A-2B, the occluding member 30 is moveable between a retracted position and a deployed position. As shown in FIG. 2A, in the retracted position, the occluding member 30 is positioned adjacent to and is attached to the first end 22 of the insertion rod 20, such that the outer surface 32 and the inner surface 34 of the occluding member 30 extend along a length of the insertion rod 20. However, as shown in FIG. 2B, in the deployed position, the insertion rod 20 assumes an umbrella-like shape with the outer surface 32 of the occluding member 30 assuming a concave shape and the inner surface 34 of the occluding member 30 assuming a convex shape, such that the occluding member 30 is then configured to provide a seal between the left atrial appendage and the left atrium of the heart. Of course, it is also contemplated that, upon deployment, the outer surface and the inner surface of the occluding member can be constructed such that the surfaces of the occluding member assume various other shapes to accommodate the anatomy of a particular heart and/or to accommodate a desired application. For example, in certain embodiments, an occluding member can include an outer surface that is convex and an inner surface that is concave. As another example, in a further embodiment, an occluding member 230 of another exemplary atrial appendage closure device 210 includes an occluding member 230 that, upon deployment, has a convex outer surface 232 and a substantially flat inner surface 234, as shown in FIGS. 7-9.

Regardless of the ultimate configuration of the occluding member upon deployment, and as perhaps best shown in FIG. 2B, the occluding member 30 is typically comprised of a flexible material or membrane 38 that is supported by a plurality of ribs 39 and/or a reinforcing mesh to thereby provide a flexible structure that is capable of being moved between a retracted and deployed position, but yet is still sufficiently rigid such that the occluding member 30 can provide an effective seal between the left atrial appendage and left atrium of a heart and will not collapse into the left atrial appendage upon being exposed to the blood flow in the heart and the pressure generated by the left atrium. In some embodiments, the occluding member is comprised of a plastic, a metal, a shape memory alloy, such as Nitinol, or combinations thereof.

With regard to the insertion rod 20 of the exemplary atrial appendage closure device 10, the insertion rod 20 is in the form of a solid rod and is generally constructed from a metal or plastic material to provide an insertion rod having a sufficient strength to allow it to be inserted into the wall of an atrial appendage of a heart and retain its shape. However, as a refinement to the atrial appendage closure devices of the presently-disclosed subject matter and, in particular, to the insertion rods of the devices, in a further embodiment, an atrial appendage closure device 210 is provided where the insertion rod 220 defines a hollow interior cavity 272 and an opening 274 at the second end 224 of the insertion rod, as shown in FIGS. 7-9. The hollow insertion rod 220 further defines a plurality of fenestrations 270 that are in fluid communication with the hollow interior cavity 272 and the opening 274 at the second end 224 of the insertion rod 220. In this regard, upon insertion of the device 210, the deployment of the occluding member 230, and the securing of the inner surface 234 and outer surface 232 of the occluding member 230 to provide a seal between the left atrial appendage 100 and the left atria of a heart, a vacuum can be applied to the opening 274 and the fenestrations 270 can be used to remove blood from the left atrial appendage 100 while also facilitating the collapsing of the left atrial appendage 100 against the inner surface 234 of the occluding member 230, as shown best in FIGS. 7-8. Similarly, by making use of the opening 274 and the fenestrations 270, radio-opaque dyes can be injected through the insertion rod 220 to check the positioning of the device 210 and the integrity of the seal provided by the device 210.

Figure 10:
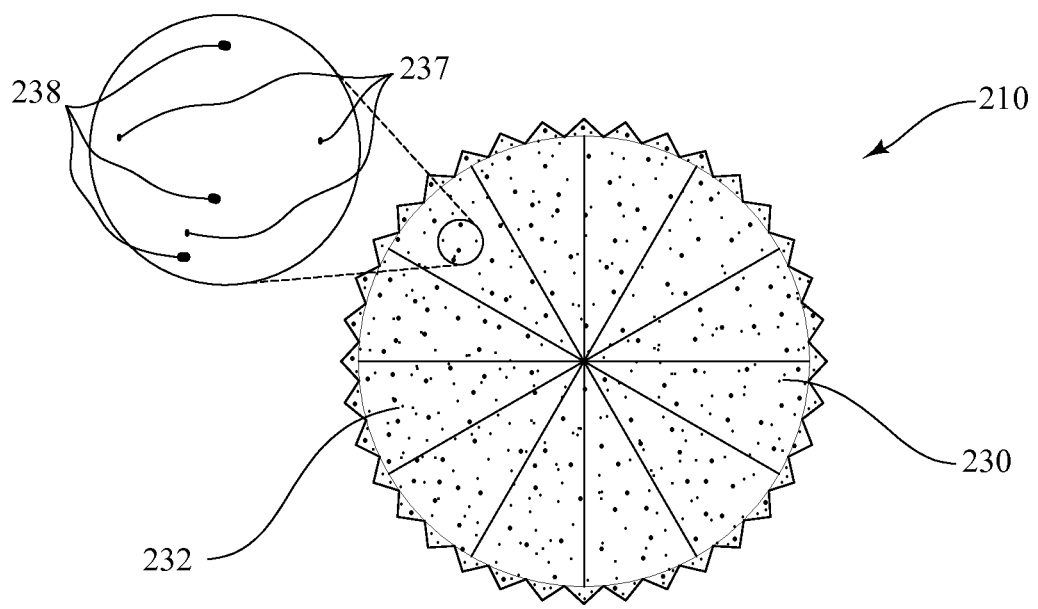
FIG. 10 is a front view of the left atrial appendage closure device shown in FIGS. 7-9, but further illustrating an extracellular matrix and growth factors coating the outer surface of the occluding member of the device.

Referring now to FIG. 10, to further facilitate the use of the atrial appendage closure device 210, the outer surface 232 of the occluding member 230 is coated with an extracellular matrix 238 and growth factors 237 using methods known to those of ordinary skill in the art. As used herein, the term "growth factor" is used to refer to a substance capable of stimulating cellular growth, proliferation, and cellular differentiation. Such growth factors include, but are not limited to, vascular endothelial growth factor (VEGF), basic fibroblast growth factor (bFGF), insulin-like growth factor (IGF), placental growth factor (PlGF), Ang1, platelet derived growth factor-BB (PDGF-BB), and transforming growth factor β (TGF-β), and combinations thereof. Of course, as would be recognized by those of ordinary skill in the art, various other materials and biological molecules can be attached to or used to coat a atrial appendage closure device of the presently-disclosed subject matter, and can be selected for a particular application as desired.

The term "extracellular matrix" is used herein to refer to the extracellular network of polysaccharides and proteins that typically serve as structural elements to the cells and tissues of a body and that provide a supporting and attachment surface for epithelial cells. In this regard, the term "extracellular matrix" is inclusive of the collection of polysaccharides and proteins that make up the extracellular matrix, but is further used to refer to the individual polysaccharides and proteins that make up the extracellular matrix, as well as the cells, such as fibroblasts and chondrocytes, that contribute to the development of the extracellular matrix. Exemplary polysaccharides and proteins of the extracellular matrix include, but are not limited to: proteoglycans, such as heparin sulfate, chondroitin sulfate, and keratin sulfate; non-proteoglycan polysaccharides, such as hyaluronic acid; collagen; elastin; fibronectin; and laminin.

Figure 5:
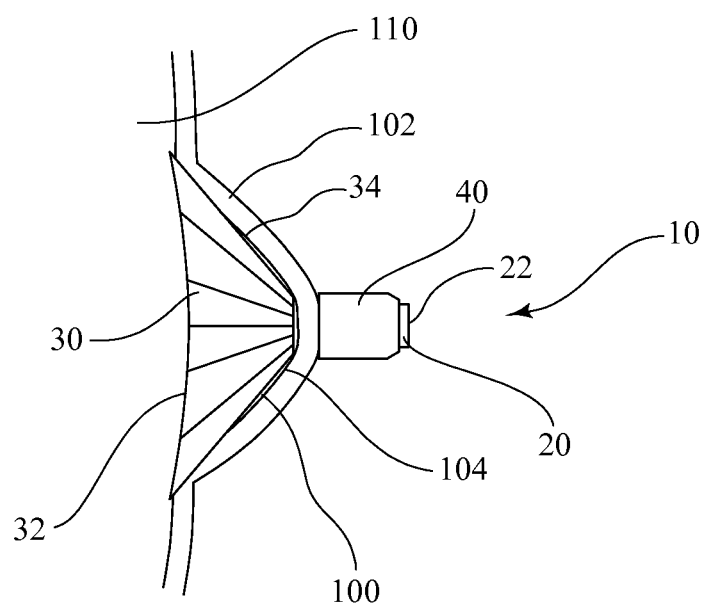
FIG. 5 is a schematic representation similar to FIGS. 3-4, but further showing the wall of the left atrial appendage completely collapsed against the inner surface of the occluding member of the atrial appendage closure device.
Figure 6:
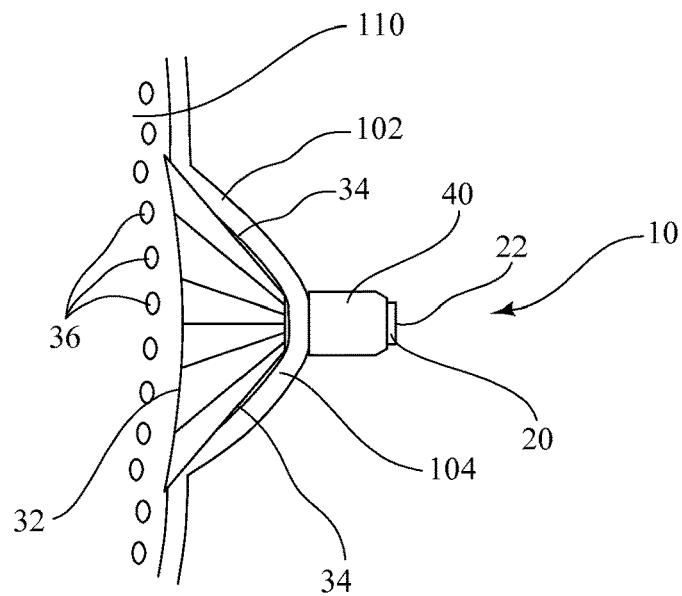
FIG. 6 is a schematic representation similar to FIGS. 3-5, but further showing an epithelial cell layer coating the outer surface of the occluding member of the atrial appendage closure device.

Referring now to FIG. 6, by including an extracellular matrix (not shown) on the occluding member 30, the device 10 can be configured so as to promote epithelialization or, in other words, to promote the deposition of epithelial cells and the growth of an epithelial cell layer 36 over the surface of the device 10. In this regard, by promoting epithelialization over the device 10, the device 10 is kept from being directly exposed to the circulating blood within the heart of a subject and scar tissue formation, immune reactions, or any other adverse events commonly associated with the implantation of a foreign body into a living subject are thereby minimized or prevented. In some embodiments, the outer surface of an exemplary occluding member is coated with an extracellular matrix, growth factors, or both to promote epithelialization or the formation of an epithelial cell layer over the entire surface of the occluding member that is placed into direct contact with the left atrium of a heart. Of course, it is also contemplated that the inner surface of an exemplary occluding member, or any other portion of an exemplary atrial appendage closure device, can also be coated with an extracellular matrix or with growth factors without departing from the spirit and scope of the subject matter described herein. For example, with reference to FIGS. 3-6, it is contemplated that the insertion rod 20 of the device 10 can be coated with an extracellular matrix such that, upon insertion of the device 10, there is not an area of the device 10 where cells are not able to adhere or where a hole may be created between the device 10 and the surrounding tissue, which may then lead to blood stasis and blood clot formation.

Referring still to FIGS. 3-6, further provided by the presently-disclosed subject matter are methods of occluding a left atrial appendage that make use of the exemplary atrial appendage closure device 10 of the presently-disclosed subject matter. In one exemplary implementation of a method of occluding a left atrial appendage in accordance with the presently-disclosed subject matter, the atrial appendage closure device 10 is first provided and, while in a retracted position, the occluding member 30 and a portion of the insertion rod 20 are inserted into the left atrial appendage 100 and the left atrium 110 by piercing the wall 102 of the left atrial appendage 100 and then pushing the occluding member 30 and the portion of the insertion rod 20 through the left atrial appendage 100 and into the left atrium 110. By making use of an occluding member 30 that is moveable between a retracted position and a deployed position, the occluding member 30 of the device 10 can advantageously be placed into its retracted position (shown in FIG. 2A) and subsequently inserted into the left atrial appendage of 100 of a heart by performing only a minimally invasive thoracotomy with a small (e.g., approximately 1 inch) incision, similar to those used in laparoscopic procedures. Of course, the device 10 can also be inserted as part of other, more invasive cardiac or vascular surgical procedures. However, without wishing to be bound by any particular theory, it is believed that by inserting the device 10 via a minimally invasive thoracotomy, implantation complications are minimized, as small thoracotomies have been shown to have less complications than other procedures that involve puncturing of the atrial septum using catheter or guidewire techniques commonly utilized in percutaneous approaches.

Figure 3:
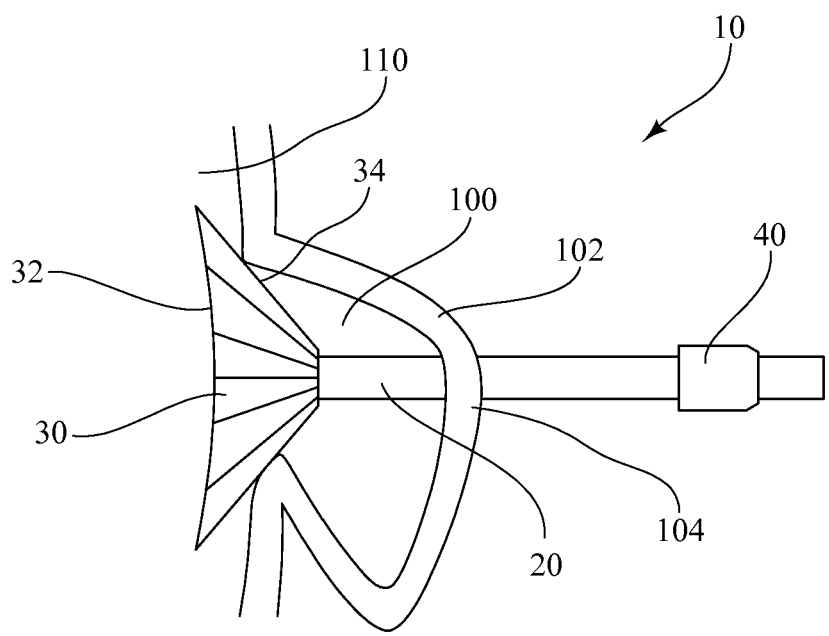
FIG. 3 is a schematic representation of an exemplary method of occluding a left atrial appendage in accordance with the presently-disclosed subject matter, in which an atrial appendage closure device of the presently-disclosed subject matter is deployed to provide a seal between the left atrial appendage and the left atrium of a heart.
Figure 4:
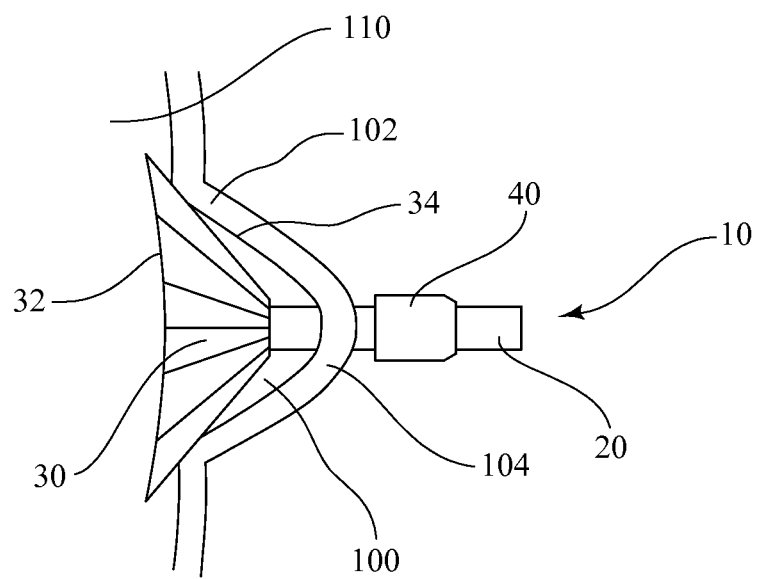
FIG. 4 is a schematic representation similar to FIG. 3, but further showing the wall of the left atrial appendage partially collapsed against the inner surface of the occluding member of the atrial appendage closure device.

Regardless of the particular surgical approach used to insert the occluding member 30 and the portion of the insertion rod 20, as shown in FIG. 3, once the occluding member 30 is inserted inside the left atrium 110, the occluding member 30 is deployed such that the outer surface 32 of the occluding member 30 assumes a concave shape, the inner surface 34 of the occluding member 30 assumes a convex shape, and the entirety of the occluding member 30 covers an area significantly beyond the opening of the left atrial appendage 100. Then, as shown in FIG. 4, while in a deployed position, the occluding member 30 and the remainder of the inserted portion of device 10 are pulled towards the tip 104 of the left atrial appendage 100. As shown in FIG. 5, the left atrial appendage 100 is then collapsed, such as by using a vacuum or other mechanical force, and the anchoring member 40 is slid along the length of the insertion rod 20 and is attached to the tip 104 of the left atrial appendage 100 to thereby completely secure the inner surface 34 of the occluding member 30 against the wall 102 of the left atrial appendage 100 and to thereby provide a complete seal between the left atrial appendage 100 and the left atrium 110 of the heart. Lastly, a portion of the insertion rod 20, including the second end 24 of the insertion rod 20 is cut away or broken at a user-defined length adjacent to the anchoring member 40 (or can be further filled with a filler to seal off the hollow interior if a hollow insertion rod is used, such as the hollow insertion rod shown in FIGS. 7-9).

Figure 11:
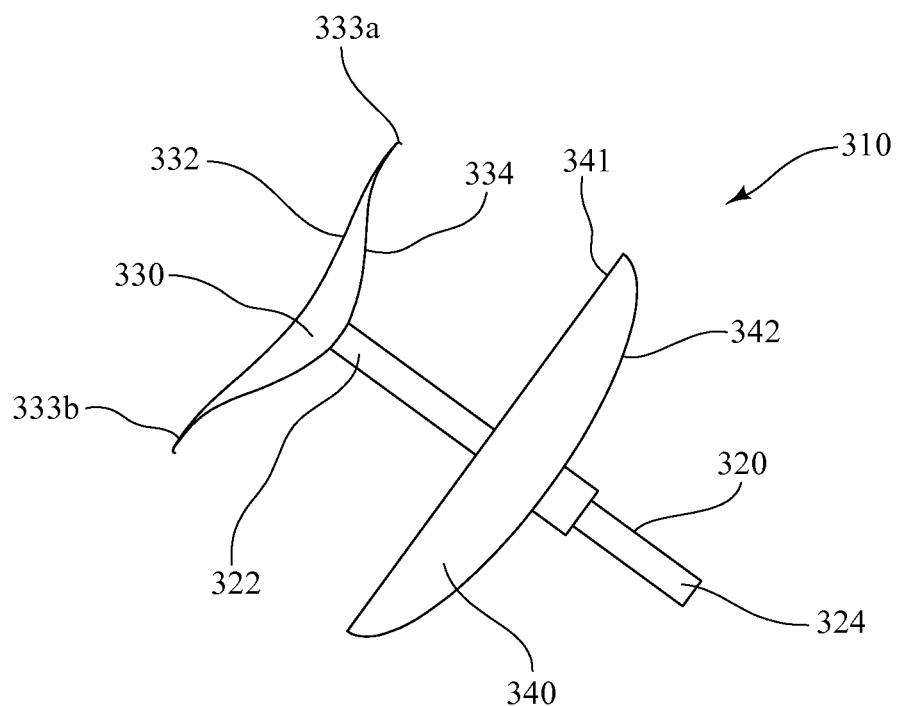
FIG. 11 is a side view of another atrial appendage closure device of the presently-disclosed subject matter, and showing the further device in a deployed position.
Figure 12A:
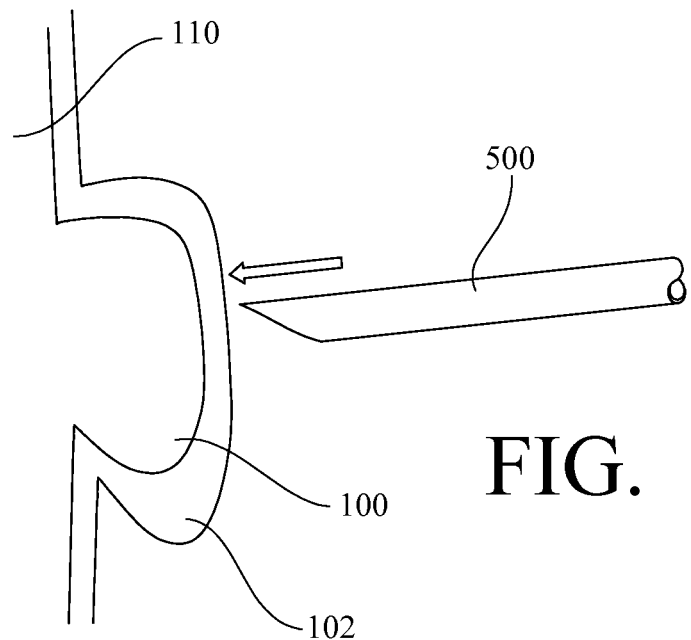
FIGS. 12A-12N are a series of schematic representations showing another exemplary method of occluding a left atrial appendage in accordance with the presently-disclosed subject matter, in which the atrial appendage closure device of FIG. 11 is used to provide a seal between the left atrial appendage and the left atrium of a heart.
Figure 12B:
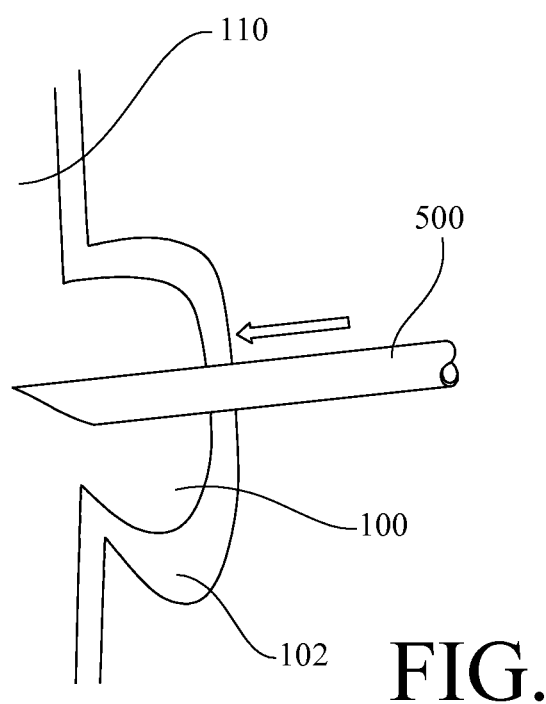
Figure 12C:
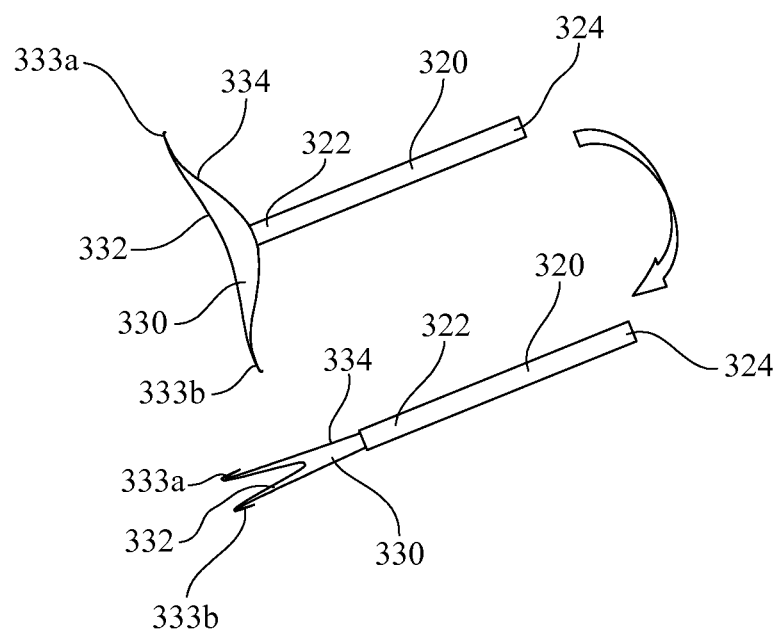
Figure 12D:
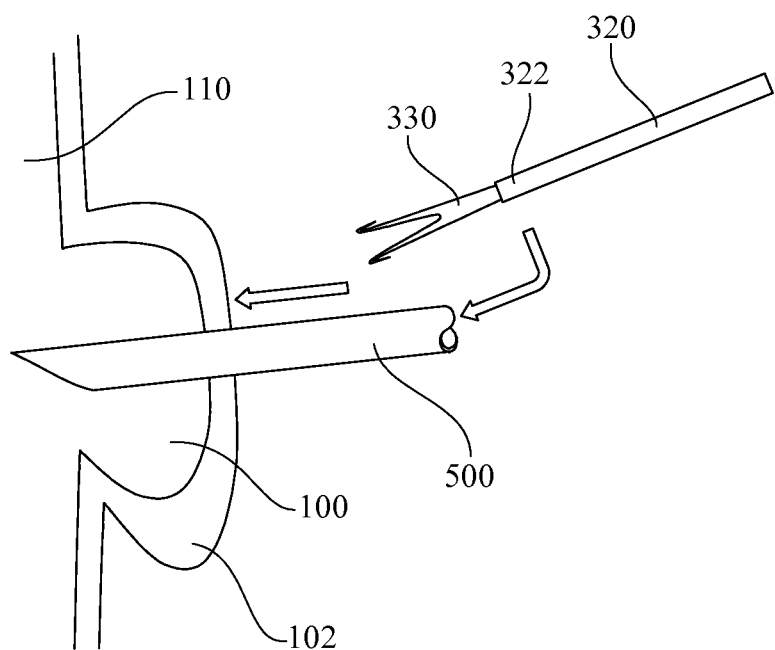
Figure 12E:
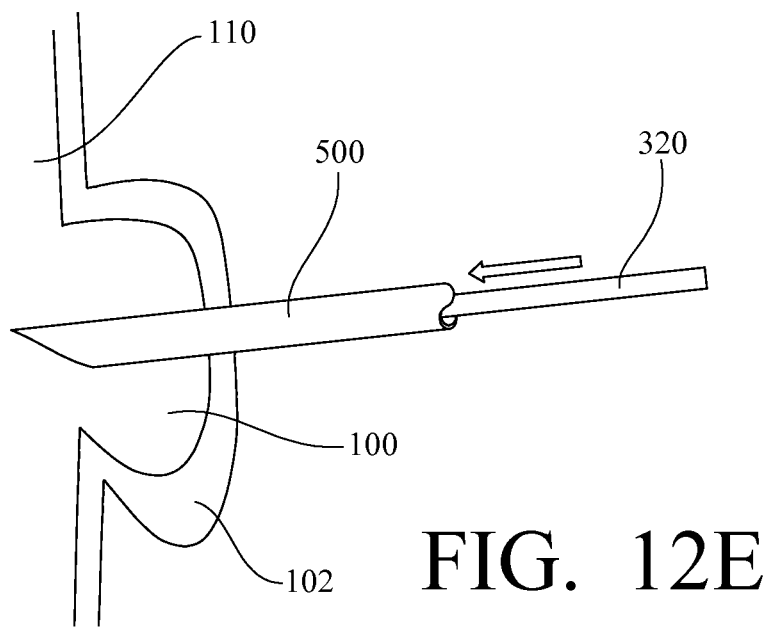
Figure 12F:
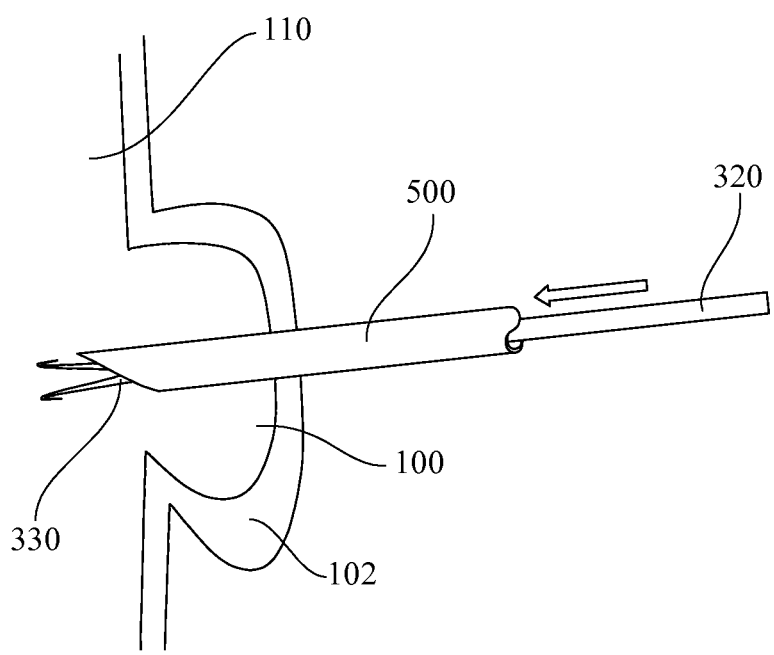
Figure 12G:
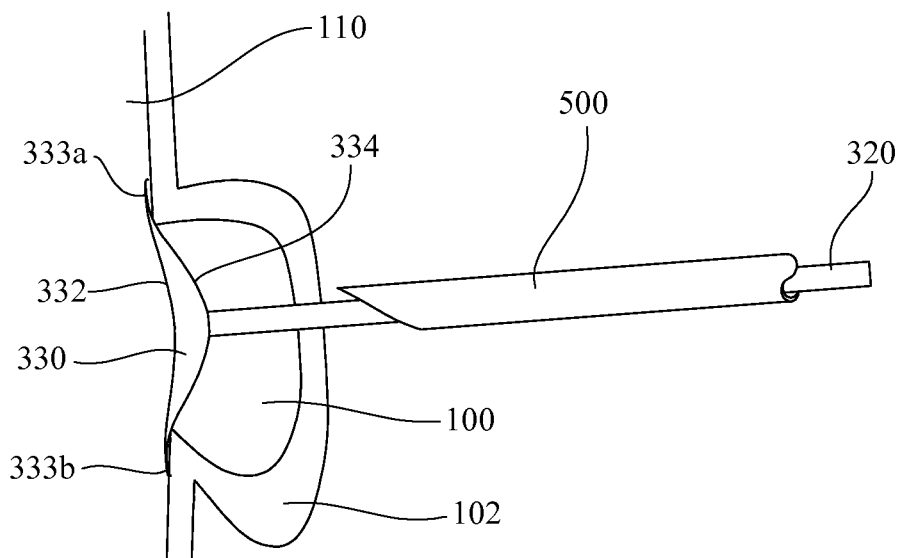
Figure 12H:
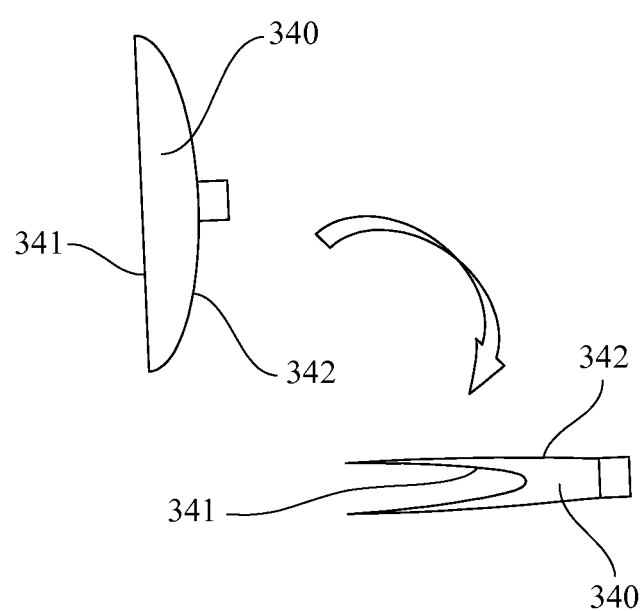
Figure 12I:
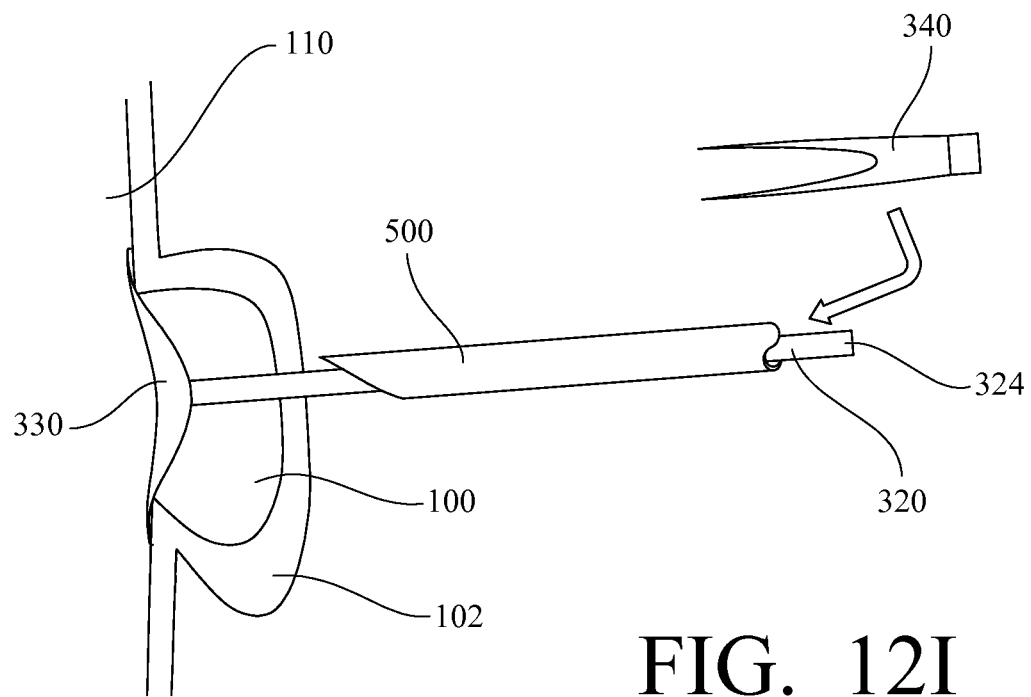
Figure 12J:
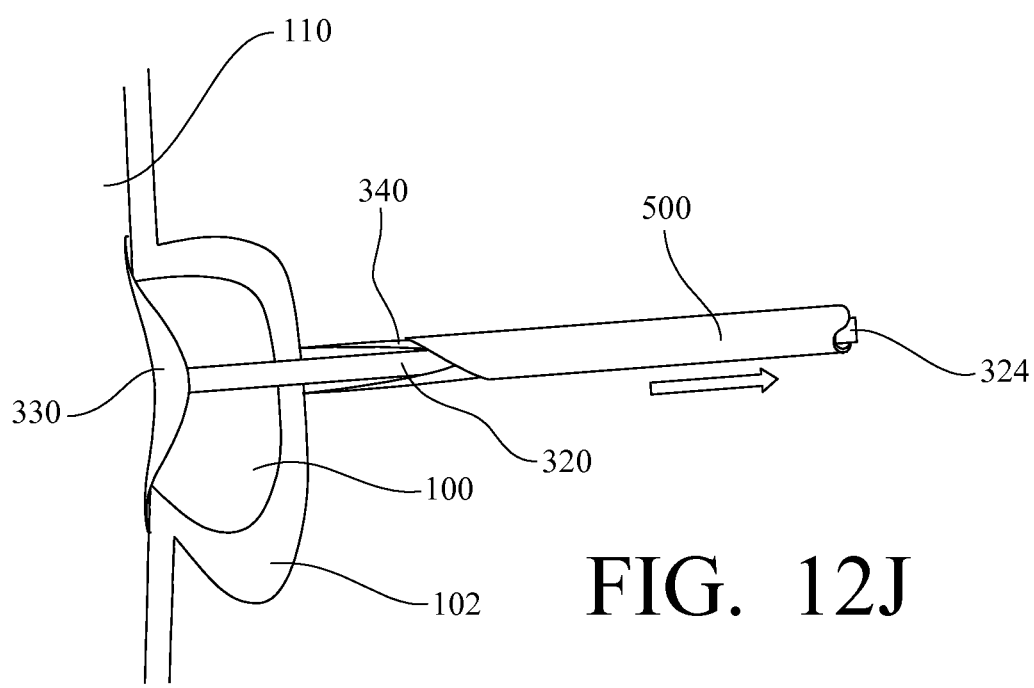
Figure 12K:
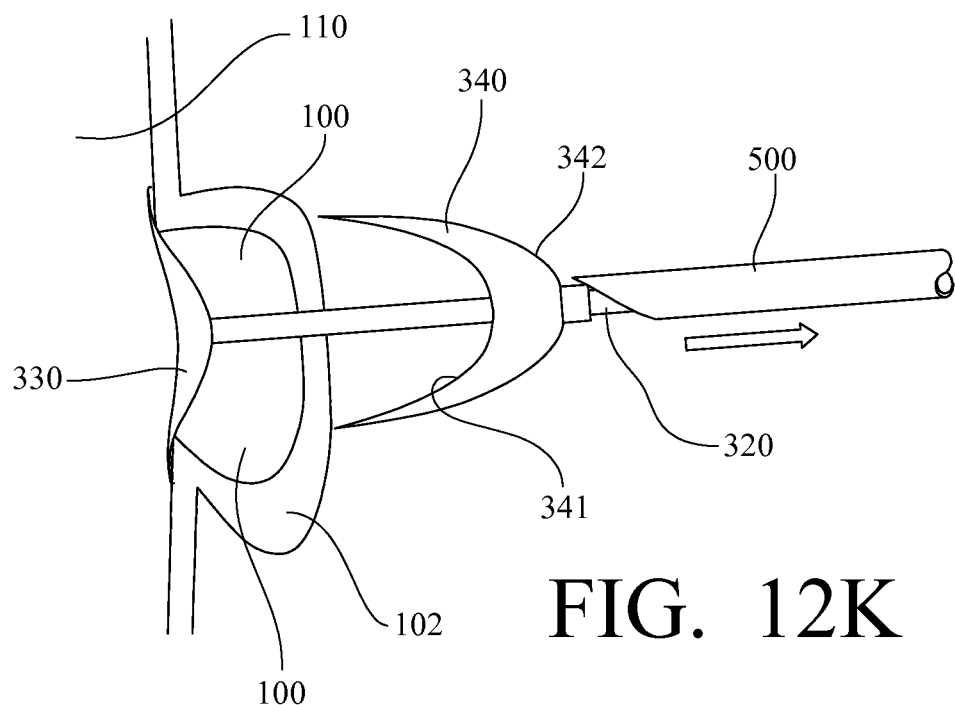
Figure 12L:
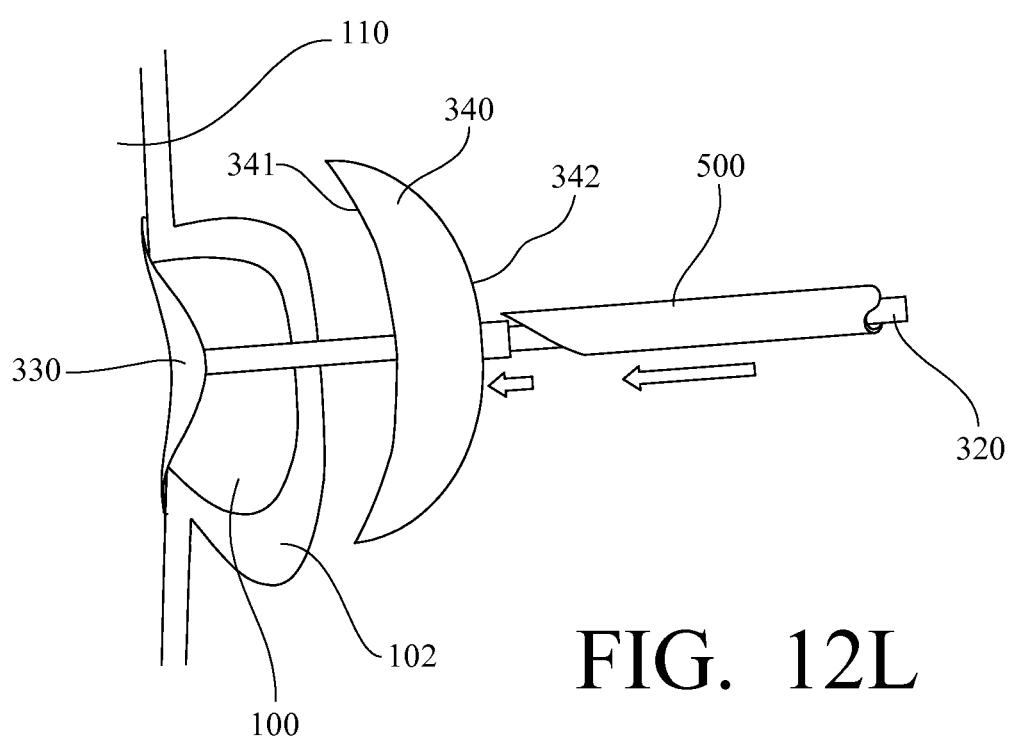
Figure 12M:
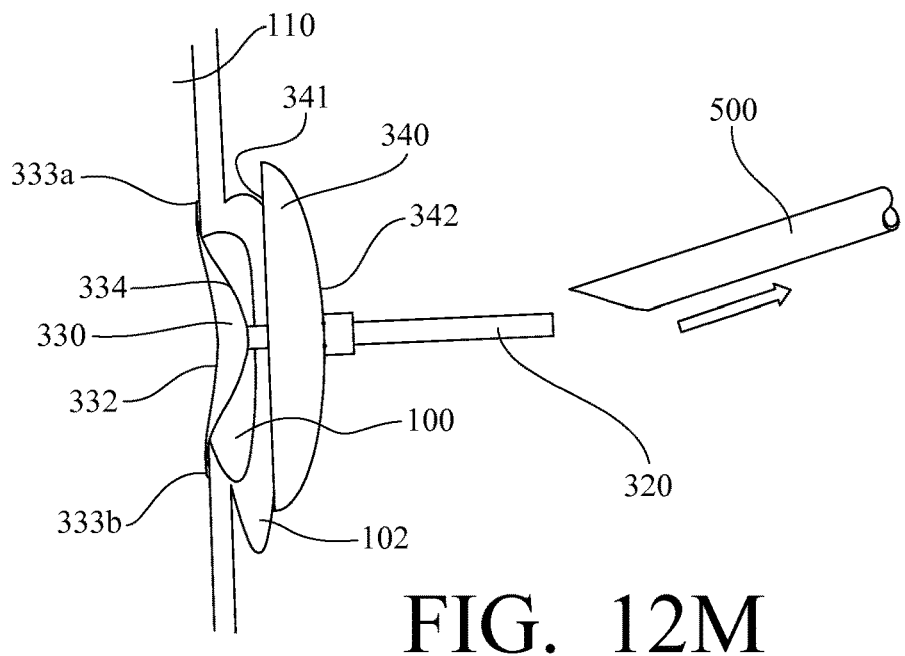
Figure 12N:
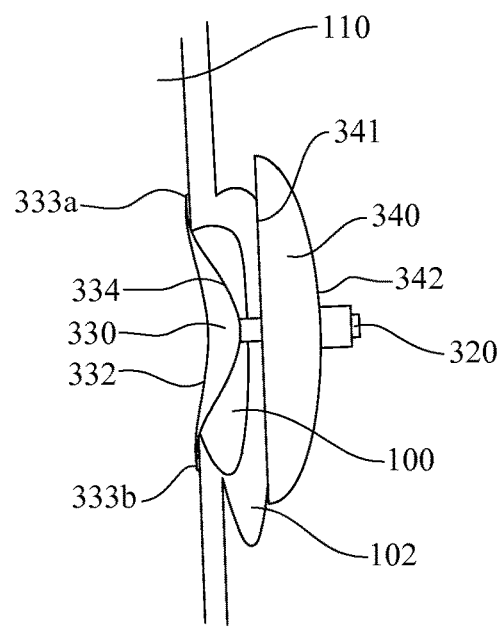

Referring now to FIGS. 11 and 12A-12N, as a refinement to the atrial appendage closure devices and methods of the presently-disclosed subject matter, an atrial appendage closure device 310 is provided that, like the atrial appendage closure devices 10, 210 shown in FIGS. 1-10, includes an insertion rod 320 having a first end 322 and a second end 324. The atrial appendage closure device 310 also includes an occluding member 330 having an outer surface 332 and an inner surface 334, and an anchoring member 340 that is connected to or otherwise attached to the insertion rod 320 for securing the device 310 to a left atrial appendage. Unlike the atrial appendage closure devices 10, 210 described above, however, the anchoring member 340 of the left atrial appendage closure device 310 is not in the form of a bolt, but rather has an umbrella-like shape, with the proximal surface 341 being substantially flat and the distal surface 342 of the anchoring member 340 having a convex shape. Additionally, the anchoring member 340 is movable between a retracted position and a deployed position, as best shown in FIG. 12H, and is configured to slide along the length of insertion rod 320. In this regard, upon the insertion of the device 310 and the insertion of the occluding member 330 into a heart to provide a seal between the left atrial appendage and the left atrium of the heart, the anchoring member 340 can be slid down the insertion rod 320 and locked to thereby collapse the left atrial appendage 100, while the increased surface area of the anchoring member 340 provides the added benefit of preventing blood from entering into the left atrial appendage 300 and clotting even if the occluding member 330 inside the left atrial appendage 100 does not completely seal off the left atrial appendage 100 from the left atrium 110.

Furthermore, with regard to the occluding member 330 of the left atrial appendage closure device 310, unlike the occluding members 30, 230 of the devices 10, 210, the occluding member 330 includes a pair of hooked end portions 333a, 333b at either end of the outer surface 332 that assist in sealing off the left atrial appendage 300 from the left atria of a heart. In this regard, it is contemplated that, in some embodiments, the occluding member 330 can further include radiating members to provide horizontal stability and circumferential members to provide circumferential stability, and, in other embodiments, can also have a biconvex structure when fully expanded so that it seals of the left atrial appendage while displaying a slightly convex surface to the inside of the heart. Additionally, it is contemplated that the occluding member 330 can be injected with a liquid or gel to retain its shape (e.g., a liquid or gel that cures or solidifies after injection setting the shape), can have a membrane or structure that is textured (e.g., roughened, flecked, or sintered) to promote formation of a native lining to minimize thromboembolic events, or can be covered with a fabric or polymeric material to promote tissue ingrowth.

In use, the atrial appendage closure device 310 is generally used in a method of occluding a left atrial appendage by first providing and inserting a large bore needle 500 through the wall 102 of a left atrial appendage 100, as shown in FIGS. 12A and 12B, respectively. The portion of the atrial appendage closure device 310 that includes only the insertion rod 320 and the occluding member 330 is then provided and the occluding member 330 is placed in a retracted position, as shown in FIG. 12C. The retracted occluding member 330 is then inserted through the large bore needle 500 along with the first end 322 of the insertion rod 320 until the occluding member 330 is sufficiently placed in the left atrium 110, as shown in FIGS. 12D-12F. The occluding member 330 is then subsequently deployed such that the outer surface 332 of the occluding member 330 assumes a convex shape, the inner surface 334 of the occluding member 330 assumes a concave shape, and the hooked end portions 333a, 333b at either end of the outer surface 332 further seal off the left atrial appendage 100 from the left atrium 110, as shown in FIG. 12G. Upon the placement of the occluding member 330, the large bore needle 500 is then retracted from the wall 102 of the left atrial appendage 100, as shown in FIG. 12G.

Subsequent to retracting the needle 500 from the wall 102 of the left atrial appendage 100, the anchoring member 340 is then provided and placed in a retracted position, as shown in FIG. 12H. The anchoring member 340 is then placed onto the second end 324 of the insertion rod 320 and is slid along the length of the insertion rod 320, as shown in FIGS. 12I-12J. Upon exiting the large bore needle 500, the anchoring member 340 is then re-deployed until the proximal surface 341 is substantially flat and the distal surface 342 of the anchoring member 340 has a convex shape, as shown in FIGS. 12K-12L. By pushing the anchoring member against the wall 102 of the left atrial appendage 100 opposite the inner surface 334 of the occluding member 330, the atrial appendage 100 is then collapsed and the large bore needle 500 is removed from the insertion rod 320, as shown in FIG. 12M. The insertion rod 320 is then cut away or otherwise broken adjacent to the anchoring member 340 to finish the occlusion of the left atrial appendage 100.

The above-described atrial appendage closure devices and related methods of occluding an atrial appendage, which allow for a left atrial appendage of a heart to be completely sealed off from the left atrium, are important both for preventing clot formation that may otherwise occur with atrial fibrillation and for minimizing surgery-related complications' that frequently occur in left atrial appendage occlusion therapy. Further, the devices of the presently-disclosed subject matter minimize the risk of puncturing portions of a heart during surgical placement as no barbs or similar anchoring mechanisms are inserted into the inside of the left atrial appendage. Moreover, the devices of the presently-disclosed subject matter can be provided in one size to thereby eliminate any patient-to-patient variability that is often observed with current atrial appendage closure devices and, in particular, pharmaceutical agent dosing. Thus, the atrial appendage closure devices of the presently-disclosed subject matter provide not only desirable alternatives to current device- or pharmaceutical agent-based therapies, with the added benefit that complications arising from the implantation of the device are minimized.

The presently-disclosed subject matter is further illustrated by the following specific but non-limiting examples. Some of the following examples are prophetic, notwithstanding the numerical values, results and/or data referred to and contained in the examples. Additionally, certain of the following examples may include compilations of data that are representative of data gathered at various times during the course of development and experimentation related to the presently-disclosed subject matter.

EXAMPLES

Example 1—Prototyping and Preliminary Testing of Atrial Appendage Closure Device Designs in Pig Hearts Eight candidate atrial appendage closure device designs are fabricated at the University of Louisville prototyping center for evaluation in pig hearts. Pig hearts are procured from slaughterhouses (Swift Slaughterhouse, Louisville) and the prototype devices are implanted. The atria of the porcine hearts are cut open and the efficacy of the prototype designs to completely occlude the left atrial appendage, the force needed to pull out the atrial appendage closure device (anchoring force), and the ease of deployment are evaluated.

Upon analysis of the results from these experiments, it is observed that the candidate designs provide complete occlusion of the left atrial appendage, with a pull out force greater than 6N (i.e., approximately the same as a suture), and are easily deployed into the a left atrial appendage. The most promising candidate designs are then selected for cadaver testing and animal experiments.

Example 2—Cadaver Fit Study

An anatomical fit study is performed in human cadavers (45-120 kg, n=4). The candidate designs are implanted using a thoracoscopic procedure. Three ports are positioned: 1 (5 mm) in the third intercostal space, 1 (10 mm) in the sixth space at the median axillary level, and 1 (10 mm) in the fifth space on the posterior axillary line. A pericardiotomy is performed parallel and posterior to the phrenic pedicle to expose the left atrial appendage. The Marshall ligament is then interrupted with electrocaudurization. Through the inferior port, the left atrial access retainer is subsequently activated with immediate step insertion and deployment of the occluding member of the device under transesophagial echocardiography guidance. The duration, ease of use, and complexity of the device is then compared with catheter-based left atrial appendage occlusion devices, and the anatomical positioning, fit and ease of occluding member deployment, and anchoring force of the devices is further evaluated.

Upon analysis of the results from these experiments, it is observed that the atrial closure devices: (1) provide complete occlusion of the left atrial appendage with a pull out force of greater than 6N; (2) can be implanted in less than 90 minutes; and (3) are rated by the surgeon as being considerably easier to insert and manipulate as compared to current catheter-based left atrial appendage occlusion techniques.

Example 3—Acute Animal Study Surgical Procedures

To begin the acute animal studies, test animals (60-100 kg, male, Jersey calves) first undergo a 14-day quarantine period. Then, the animals are anesthetized with 1-5% isoflurane and 100% oxygen, and a left thoracotomy is performed at the 5th intercostal space to provide access and exposure of the left atrial appendage. Heparin (200-300 units/kg via IV central line) is administered and the atrial appendage closure device of the presently-disclosed subject matter is implanted as described herein above. Echocardiography is performed on each calf to verify anatomical positioning and fit of the closure device. Fluoroscopy is also performed to confirm anatomical positioning of the closure device during implantation. In this regard, a vascular sheath is placed in the carotid artery, and an angiography catheter may be placed in the left atrium for injection of radiopaque dye (100-150 mL, which may be repeated 3-5 times) for flow visualization during fluoroscopy. After the evaluation period, at necropsy, full gross examination of end organs is completed, with particular attention on the left atrial appendage area, where the device is further visually inspected for fit, positioning, and evidence of clots or defects.

Upon analysis of the results from these studies, it is again observed that the devices of the presently-disclosed subject matter: (1) provide complete occlusion of left atrial appendage with a pull out force of greater than 6N; (2) can be implanted in less than 90 minutes; (3) are rated by the surgeon as being considerably easier to insert and manipulate as compared to current catheter-based left atrial appendage occlusion techniques; and (4) allow for blood loss to be less than 100 ml during implantation.

Example 4—Chronic Animal Study Surgical Procedures

For the chronic animal studies using the devices of the presently-disclosed subject matter, the quarantine, anesthesia, and implantation techniques used in the acute studies are again employed to place the device in the left atrial appendage of the test animals (60-100 kg, male, Jersey calves). In the chronic animal studies, echocardiography and fluoroscopy are performed at the beginning and end of the 14-day chronic study period. Histopathological analyses are performed on the device surface and the left atrial appendage to quantify endothelialization of device surface, tissue ingrowth, and device-related injury Upon analyzing the results from the chronic animal studies, it is observed that the devices of the presently-disclosed subject matter: (1) provide complete occlusion of the left atrial appendage with a pull out force greater than 6N without device fracture or failure; (2) are capable of being implanted in less than 90 minutes; (3) are rated by the surgeon as being considerably easier to insert and manipulate as compared to current catheter-based left atrial appendage occlusion techniques; (4) allow for blood loss to be less than 100 ml during implantation; (5) exhibit no blood leaks at the device-left atrial appendage junction over the duration of the study; (6) show no visible device migration; (7) result in no visible injury to the myocardium or embolization in the end-organs in of the animals; and (8) allow for full endothelialization of the device surface with no or minimal histopathological damage to the myocardium, thus indicating that the devices of the presently-disclosed subject matter can effectively be used as part of a method for occluding the left atrial appendage of a heart.

Throughout this document, various references are mentioned. All such references are incorporated herein by reference, including the references set forth in the following list:

REFERENCES

1. Atrial Fibrillation Fact Sheet. February 2010. Centers for Disease Control and Prevention. 3 Apr. 2012.
2. Go A S, Hylek E M, Phillips K A, Chang Y, Henault L E, Shelby J V and Singer D E. Prevalence of Diagnosed Atrial Fibrillation in Adults: National Implications for Rhythm Management and Stroke Prevention: the Anticoagulation and Risk Factors in Atrial Fibrillation (Atria) Study. *Journal of the American Medical Association* 2001; 285:2370-2375.
3. Wolf P A, Abbott R D, and Kannel W B. Atrial fibrillation as an Independent factor for stroke: The Framingham study. Stroke; 1991; 22:983-988.
4. Pearce L A, Hart R G and Halperin M. Assessment of Three Schemes for Stratifying Stroke Risk in Patients with Nonvalvular Atrial Fibrillation. *The American Journal of Medicine* 2000; 109:45-51.
5. Aronow W S. Management of the Older Person With Atrial Fibrillation. *Journal of Gerontology: Medical Sciences* 2002; 57A:M352-M363.
6. Savelieva I, Bajpai A and Camm A J. Stroke in atrial fibrillation: Update on pathophysiology, new antithrombotic therapies, and evolution of procedures and devices. *Annals of Medicine* 2007; 39:371-391.
7. Jais P, Haissaguerre M, Shah D C, Chouairi S, Gencel L, Hocini M, and Clementy J. A Focal Source of Atrial Fibrillation Treated by Discrete Radiofrequency Ablation. *Circulation.* 1997; 95:572-576.
8. Go A S, Hylek E M, Borowsky L H, Phillips K A, Selby T V and Singer D E. Warfarin Use among Ambulatory Patients with Nonvalvular Atrial Fibrillation: The Anticoagulation and Risk Factors in Atrial Fibrillation (Atria) Study. *Annals of Internal Medicine* 1999; 131:927-934.
9. Mendelson G, and Aronow W S. Underutilization of Warfarin in Older Persons with Chronic Nonvalvular Atrial Fibrillation at High Risk for Developing Stroke. *Journal of the American Geriatrics Society* 1998; 46:P1423-P1424.
10. Hart R G, Benavente O, McBride R and Pearce L A. Antithrombotic Therapy To Prevent Stroke in Patients with Atrial Fibrillation: A Meta-Analysis. *Annals of Internal Medicine* 1999; 131:492-501.

11. Hylek E M, Go A S, Chang Y, Jensvold N G, Henault L E, Selby T V, et al. Effect of intensity of oral anticoagulation on stroke severity and mortality in atrial fibrillation. N Engl J Med. 2003; 349:1019-26.
12. Nieuwlaat R, Capucci A, Lip G Y, Olsson S B, Prins M H, Nieman F H, et al.; Euro Heart Survey Investigators. Antithrombotic treatment in real-life atrial fibrillation patients: a report from the Euro Heart Survey on Atrial Fibrillation. Eur Heart J. 2006; 27:3018-26.
13. McCormick D, Gurwitz J H, Goldberg R J, Becker R, Tate J P, Elwell A, et al. Prevalence and quality of warfarin use for patients with atrial fibrillation in the long-term care setting. Arch Intern Med. 2001; 16:2458-63.
14. Sarawate C, Sikirica M V, Willey V J, Bullano M F, Hauch O. Monitoring anticoagulation in atrial fibrillation. J Thromb Thrombolysis. 2006; 21:191-8.
15. Singer D E, Albers G W, Dalen J E, Go A S, Halperin J L, and Manning W J. Antithrombotic therapy in atrial fibrillation: the Seventh ACCP Conference on Antithrombotic and Thrombolytic Therapy. *Chest* 2004; 126:429S-56S.
16. Risk factors for stroke and efficacy of antithrombotic therapy in atrial fibrillation. Analysis of pooled data from five randomized controlled trials. *Archives of Internal Medicine* 1994; 154:1449-57.
17. Atwood J E, and Albers G W. Anticoagulation and atrial fibrillation. *Herz* 1993; 18:27-38
18. Gullov A L, Koefoed B G, and Petersen P. Bleeding During Warfarin and Aspirin Therapy in Patients With Atrial Fibrillation: The Afasak 2 Study. *Archives of Internal Medicine* 1999; 159:1322-1328.
19. Liu M, Counsell C, Sandercock P. Anticoagulants for preventing recurrence following ischaemic stroke or transient ischaemic attack. (Cochrane Review). In: The Cochrane Library, Issue 1, 2002. Oxford: Update Software.
20. Desbiens D A. Deciding on Anticoagulating the Oldest Old with Atrial Fibrillation: Insights from Cost-Effectiveness Analysis. JAGS 2002; 50:863-869.
21. Aronow W S, Ahn C, Kronzon I, and Gutstein H. Incidence of new thromboembolic stroke in persons 62 years and older with chronic atrial fibrillation treated with warfarin versus aspirin. *Journal of the American Geriatrics Society* 1999; 47:366-8.
22. Lip G Y. Aspirin for Prevention of Stroke in Atrial Fibrillation. *Stroke* 2006; 37:1640.
23. Garcia D, and Hylek E. Stroke prevention in elderly patients with atrial fibrillation. *The Lancet* 2007; 370:460-461.
24. Lip G Y H and Boos C J. Antithrombotic treatment in atrial fibrillation. *Heart* 2006; 92:155-161.
25. Jaffer A K. Warfarin reduced major stroke more than aspirin in elderly patients with atrial fibrillation in primary care. *Evidence Based Medicine* 2007; 12:172.
26. Kamath S, Blann A D, Chin B S, Lip G Y. A prospective randomized trial of aspirin-clopidogrel combination therapy and dose-adjusted warfarin on indices of thrombogenesis and platelet activation in atrial fibrillation. J Am Coll Cardiol. 2002; 40:484-90.
27. Lorenzoni R, Lazzerini G, Cocci F, De Caterina R. Shortterm prevention of thromboembolic complications in patients with atrial fibrillation with aspirin plus clopidogrel: the Clopidogrel-Aspirin Atrial Fibrillation (CLAAF) pilot study. Am Heart J. 2004; 148:e6.
28. ACTIVE Writing Group on behalf of the ACTIVE Investigators; Connolly S, Pogue J, Hart R, Pfeffer M, Hohnloser S, Chrolavicius S, et al. Clopidogrel plus aspirin versus oral anticoagulation for atrial fibrillation in the Atrial fibrillation Clopidogrel Trial with Irbesartan for prevention of Vascular Events (ACTIVE W): a randomized controlled trial. Lancet. 2006; 367:1903-12.
29. Healey J, Hart R, Pogue J, Yusuf S, Pfeffer M, Hohnloser S, et al., on behalf of The ACTIVE-W Investigators. Effect of underlying risk of stroke on treatment effects in the ACTIVEW Trial. (Abstract). Eur Heart J. 2006; 27 Supplement: Abstract P451.
30. Perzborn E, Roehrig S, Straub, A, Dagmar K, Mueck W, and Laux V. Rivaroxaban: A new oral factor Xa inhibitor. Arteriosclerosis, Thrombosis, and Vascular Biology. 2010; 30:376-381
31. Eriksson B, Quinlan D, Weitz J. Comparative Pharmacodynamics and Pharmacokinetics of oral direct thrombin and Factor Xa inhibitors in development. Clinical Pharmacokinetics 2009: 48: 1-22.
32. Bayard Y L, Ostermayer S H, Hein R, Skowasch M, Buscheck F, Baranowski A, Heinisch C, Sievert H. Percutaneous devices for stroke prevention. Cardiovascular Revascularization Medicine. 2007:8:216-225.
33. Hanna I R, Kolm P, Martin R, Reisman M, Gray W and Block P C. Left atrial structure and function after percutaneous left atrial appendage transcatheter occlusion (PLAATO): Six-month echocardiographic follow-up. *Journal of the American College of Cardiology* 2004; 43:1868-72.
34. Nakai T, Lesh M D, Gerstenfeld E P, Virmani R, Jones R and Lee R J. Percutaneous Left Atrial Appendage Occlusion (PLAATO) for Preventing Cardioembolism: First Experience in Canine Model. *Circulation* 2002; 105:2217-2222.
35. Ostermayer S H, Reisman M, Kramer P H, Matthews R V, Gray W A, Block P C, Omran H, Bartorelli A L, Bella P D, Mario C D, Pappone C, Casale P N, Moses J W, Poppas A, Williams D O, Meier B, Skanes A, Teirstein P S, Lesh M D, Nakai T, Bayard Y, Billinger K, Trepels T, Krumsdorf U, and Sievert H. Percutaneous Left Atrial Appendage Transcatheter Occlusion (PLAATO System) to Prevent Stroke in High-Risk Patients With Non-Rheumatic Atrial Fibrillation: Results From the International Multi-Center Feasibility Trials. Journal of the American College of Cardiology 2005; 46:9-14.
36. Sievert H, Lesh M D, Trepels T, Omran H, Bartorelli A, Bella P D, Nakai T, Reisman M, DiMario C, Block P, Kramer P, Fleschenberg D, Krumsdorf U, and Scherer D. Percutaneous Left Atrial Appendage Transcatheter Occlusion to Prevent Stroke in High-Risk Patients With Atrial Fibrillation: Early Clinical Experience. *Circulation* 2002; 105:1887-1889.
37. Fountain R B, Holmes D R, Chandrasekaran K, Packer D, Asirvatham S, Tassel R V and Turi Z. The Protect A F (Watchman Left Atrial Appendage System for Embolic Protection in Patients with Atrial Fibrillation) Trial. *American Heart Journal* 2006; 151:956-61.
38. Sick P B, Schuler G, Hauptmann K E, Grube E, Yakubov S, Turi Z G, Mishkel G, Almany S, and Holmes D R. Initial Worldwide Experience with the WATCHMAN Left Atrial Appendage System for Stroke Prevention in Atrial Fibrillation. *Journal of the American College of Cardiology* 2007; 49:1490-5.
39. Sievert H and Bayard Y L. Percutaneous closure of the left atrial appendage: A major step forward. J Am Coll Cardiol Intv, 2009; 2:601-602.
40. Block P C. Watching the WATCHMAN. J Am Coll Cardiol, 2007; 49:1496-1497.

41. Maisel W H. Left atrial appendage occlusion—closure or just the beginning. New England Journal of Medicine, 2009.
42. Sick P B, Schuler G, Hauptmann K E, et al (April 2007). "Initial worldwide experience with the WATCHMAN left atrial appendage system for stroke prevention in atrial fibrillation". *J Am. Coll. Cardiol.* 49 (13):1490-5
43. Onalan O and Crystal E. Left Atrial Appendage Exclusion for Stroke Prevention in Patients With Nonrheumatic Atrial Fibrillation. *Stroke* 2007; 38:624-630.
44. Ailawadi G, Gerdisch M W, Harvey R L, Hooker R L, Damiano R J Jr, Salamon T, and Mack M J. Exclusion of the left atrial appendage with a novel device: early results of a multicenter trial. *J Thorac Cardiovasc Surg.* 2011; 142(5):1002-9.
45. Payne K A, Huybrechts K F, Caro J J, Craig Green T J, Klittich W S. Long term cost-of-illness in stroke: an international review. Pharmacoeconomics. 2002; 20:813-25.
46. Lafata J E, Martin S A, Kaatz S, Ward R E. The cost effectiveness of different management strategies for patients on chronic warfarin therapy. J Gen Intern Med. 2000; 15:31-7.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An atrial appendage closure device, comprising:
   an insertion rod having a first end and a second end;
   an occluding member connected to the first end of the insertion rod such that the insertion rod terminates at the occluding member, the occluding member including a plurality of ribs, the occluding member having an outer surface positioned away from the insertion rod and an inner surface positioned adjacent the insertion rod with the outer surface of the occluding member having a hooked portion at each end of the outer surface, and the occluding member being moveable between a retracted position and a deployed position, wherein, in the deployed position, the occluding member is configured to provide a seal between a left atrial appendage and a left atrium of a heart; and
   an anchoring member connected to an outside of the insertion rod and configured to slide along the outside of the insertion rod for securing the device to a wall of the left atrial appendage; and
   the outer surface of the occluding member assumes a convex shape and the inner surface of the occluding member assumes a flattened shape.

2. The device of claim 1, wherein the outer surface, the inner surface, or both the outer surface and the inner surface of the occluding member are coated with an extracellular matrix.

3. The device of claim 1, wherein the outer surface, the inner surface, or both the outer surface and the inner surface of the occluding member are coated with a growth factor.

4. The device of claim 1, wherein the occluding member comprises a flexible membrane supported by the plurality of ribs.

5. The device of claim 1, wherein the anchoring member has a substantially flat proximal surface and a convex distal surface.

6. The device of claim 1, wherein the anchoring member is movable between a retracted position and a deployed position.

7. The device of claim 1, wherein the insertion rod defines a hollow interior cavity and an opening at the second end of the insertion rod, and wherein the insertion rod further defines a plurality of fenestrations in fluid communication with the hollow interior cavity and the opening at the second end of the insertion rod.

8. A method of occluding a left atrial appendage, comprising:
   providing a closure device including,
   an insertion rod having a first end and a second end, and
   an occluding member connected to the first end of the insertion rod such that the insertion rod terminates at the occluding member, the occluding member including a plurality of ribs, the occluding member having an outer surface positioned away from the insertion rod and an inner surface positioned adjacent the insertion rod with the outer surface of the occluding member having a hooked portion at each end of the outer surface, and the occluding member being moveable between a retracted position and a deployed position, and an anchoring member connected to an outside of the insertion rod and configured to slide along the outside of the insertion rod for securing the device to a wall of the left atrial appendage;
   inserting the occluding member and a portion of the insertion rod into the left atrial appendage and into a left atrium of a heart while the occluding member is in a retracted position;
   deploying the occluding member inside the left atrium such that the occluding member is configured to provide a seal between the left atrial appendage and the left atrium of the heart;
   securing the inner surface of the occluding member against a wall of the left atrial appendage to thereby provide a seal between the left atrial appendage and the left atrium of the heart; and
   securing the anchoring member to the wall of the left atrial appendage; and
   the outer surface of the occluding member assumes a convex shape and the inner surface of the occluding member assumes a flattened shape.

9. The method of claim 8, wherein the step of securing the inner surface of the occluding member against the wall of the left atrial appendage comprises pulling the occluding member toward a tip of the left atrial appendage subsequent to deploying the including member inside the left atrium.

10. The method of claim 8, wherein the step of securing the inner surface of the occluding member against the wall of the left atrial appendage comprises collapsing the wall of the left atrial appendage against the inner surface of the occluding member.

11. The method of claim 8, wherein the step of inserting the occluding member and the portion of the insertion rod into the left atrial appendage and the left atrium comprises:
   piercing the wall of the left atrial appendage; and
   inserting the occluding member and the portion of the insertion rod through the wall of the left atrial appendage.

12. The method of claim 11, wherein the step of piercing the wall of the left atrial appendage comprises piercing the wall of the left atrial appendage with a hollow needle.

13. The method of claim 12, wherein the step of inserting the occluding member and the portion of the insertion rod through the wall of the left atrial appendage comprises inserting the occluding member and the portion of the insertion rod through the hollow needle and into the left atrial appendage and the left atrium.

14. The method of claim 8, wherein securing the anchoring member to the wall of the left atrial appendage includes moving the anchoring member between a retracted position and a deployed position.

15. The method of claim 8, wherein securing the anchoring member to the wall of the left atrial appendage includes:
- inserting the anchoring member through the hollow needle;
- deploying the anchoring member adjacent to the wall of left atrial appendage; and
- securing the anchoring member to the wall of the left atrial appendage opposite the occluding member.

\* \* \* \* \*